United States Patent [19]

Huang et al.

[11] Patent Number: 5,210,208

[45] Date of Patent: May 11, 1993

[54] DISUBSTITUTED ARYL COMPOUNDS EXHIBITING SELECTIVE LEUKOTRIENE B4 ANTAGONIST ACTIVITY

[75] Inventors: Fu-Chih Huang, Gwynedd; Wan K. Chan, Wayne; Charles A. Sutherland, Greenlane; Robert A. Galemmo, Jr., Collegeville; Michael N. Chang, Newton, all of P.A.

[73] Assignee: Rhone-Poulenc Rorer Pharmaceuticals Inc., Collegeville, Pa.

[21] Appl. No.: 586,830

[22] Filed: Sep. 24, 1990

[51] Int. Cl.$^5$ .................. C07D 257/04; A61K 31/41; A61K 31/16; C07E 223/07

[52] U.S. Cl. .................... 548/253; 562/455; 548/252

[58] Field of Search ............... 548/252, 253; 514/381, 514/617, 621

[56] References Cited

U.S. PATENT DOCUMENTS

| | | | |
|---|---|---|---|
| 4,727,180 | 2/1988 | Aldrich et al. | 514/617 |
| 4,820,722 | 4/1989 | Carr et al. | 548/253 |
| 5,140,046 | 8/1992 | Mase et al. | 562/455 |

*Primary Examiner*—David B. Springer
*Attorney, Agent, or Firm*—James A. Nicholson; Martin F. Savitzky

[57] ABSTRACT

Monocyclic and bicyclic aryl ring compounds having selective LTB$_4$ properties and comprising two ring substituents, the first substituent comprising a lipophilic group and a terminal carboxylic acid or derivative group, and the second substituent comprising an amido group, therapeutic compositions and methods of treatment of disorders which result from LTB$_4$ activity using the mono- and bicyclic aryl compounds are disclosed.

20 Claims, No Drawings

DISUBSTITUTED ARYL COMPOUNDS EXHIBITING SELECTIVE LEUKOTRIENE B4 ANTAGONIST ACTIVITY

FIELD OF THE INVENTION

The present invention relates to a class of novel compounds useful in the treatment of a variety of diseases that involve undesirable inflammatory or hypersensitivity responses in diverse animal tissues. Approaches to the treatment of these responses have been as varied as the tissues in which such responses take place, and include the administration of antihistamines, analgesics such as aspirin, topical coal tar as well as others.

A more recent approach to the moderation of inflammatory and hypersensitivity responses has focused on blocking the action of arachidonic acid metabolites (including the prostaglandins), lipoxygenases and the leukotrienes. The leukotrienes (LT) metabolites are formed by oxygenation of a lipoxygenase (5-hydroperoxy-tetraenoic acid (5-HPETE)) which is formed by the specific oxygenation of the C-5 position of arachidonic acid. The first leukotriene formed in the metabolic pathway is the unstable epoxide intermediate leukotriene $A_4$ ($LTA_4$) which is the precursor to the family of peptido-leukotrienes, the first in the pathway being $LTC_4$ which is formed by glutathione addition. $LTC_4$ is transformed subsequently into $LTD_4$ and $LTE_4$ by successive elimination of a glutamyl and glycine residue. The peptido-leukotrienes primarily act on smooth muscle and other cells having contractile capacity, as well as playing a key role in hypersensitivity reactions. In addition, the peptido-leukotrienes are spasmogens, increase vascular permeability, activate airway smooth muscle, stimulate mucous secretion and are involved with the pathogenesis of certain inflammatory diseases such as bronchitis, ectopic and atopic eczema and psoriasis. Leukotrienes appear to be involved in the pathogenesis of asthma such as allergic pulmonary disorders of asthma, hay fever and allergic rhinitis. In addition, $LTC_4$, $LTD_4$ and $LTE_4$ may also decrease blood pressure by an action on the heart, because they reduce myocardial contractility and coronary blood flow.

Another family of leukotrienes, the $LTB_4$, is derived from $LTA_4$ by hydrolase-catalyzed addition of water. This 5,12-dihydroxy derivative, causes adhesion and chemotactic movement of leukocytes, stimulates aggregation, enzyme release and generation of superoxide in neutrophils. Additionally, $LTB_4$ is a potent chemotactic and chemokinetic agent for eosinophils, macrophages and monocytes, stimulates suppressor T lymphocytes and enhances natural cytotoxic cell activity. $LTB_4$ is also a potent (indirect) bronchoconstrictor but in contrast to the peptidoleukotrienes $C_4$, $D_4$ and $E_4$ does not appreciably stimulate mucous production and induce edema of the airways by increasing vascular permeability.

Reported Developments

It has been suggested that compounds antagonizing $LTB_4$ activity may be valuable in the treatment of inflammatory diseases caused by tissue degrading enzymes and reactive chemicals liberated by tissue-infiltrating and aggregating polymorphonuclear leukocytes. Such disease states include inflammatory bowel disease, reperfusion injury, chronic lung diseases, various arthritic conditions, inflammatory conditions associated with asthma (such as late phase hypersensitivity) and psoriasis.

The literature reports a variety of compounds exhibiting leukotriene $B_4$ antagonist activity. These include compounds having chemical structures mimicking leukotriene structures such as Sumitomo's SM 9064, UpJohn's U-75360 and U-75302 and Ciba Geigy's CGS 23113. Other compounds, some of which include monocyclic ring structures and which are disclosed in EP 276064, EP 276065 and EP 292977, are reported to exhibit both $LTD_4$ and $LTB_4$ antagonist properties.

The present invention is directed to a class of novel bicyclic ring containing compounds which exhibit selective $LTB_4$ antagonist activity.

SUMMARY OF THE INVENTION

This invention relates to compounds having $LTB_4$ antagonist properties and to therapeutic compositions and methods for the treatment of disorders which result from $LTB_4$ activity. In general, this invention comprises mono- and bicyclic aryl compounds having selective $LTB_4$ antagonist properties and comprising at least two substituents attached to the aryl ring having three functional groups present thereon; an amido function, a terminal carboxylic acid or derivative thereof function and a lipophilic function.

DETAILED DESCRIPTION AND PREFERRED EMBODIMENTS

As employed above and throughout this disclosure, the following terms, unless otherwise indicated, shall be understood to have the following meanings:

"Bicyclic aryl" means a bicyclic ring system composed of two fused rings which may be partially or completely unsaturated carbocyclic and/or heterocyclic rings. Preferred bicycles include naphthalene, indole, benzothiophene, benzofuran, quinoline, chromone and purine.

"Monocyclic aryl" means a partially or completely unsaturated carbocyclic and/or heterocyclic ring. Preferred monocycles include benzene, thiophene, pyridine, furan and pyrimidine.

"Aryl" refers to a partially or completely unsaturated carbocyclic or heterocyclic aromatic ring.

"Alkyl", either alone or with various substituents defined herein, means a saturated aliphatic hydrocarbon, either branched- or straight-chained. A "loweralkyl" is preferred having about 1 to about 6 carbon atoms. Examples of alkyl include methyl, ethyl, n-propyl, isopropyl, butyl, sec-butyl, t-butyl, amyl and hexyl.

"Alkoxy" refers to a loweralkyl-O-group.

"Alkenyl" refers to a hydrocarbon having at least one point of unsaturation and may be branched- or straight-chained. Preferred alkenyl groups have 2 to about 6 carbon atoms present. Exemplary alkenyl groups include vinyl, allyl, ethynyl and isopropenyl.

The preferred aryloxy group is phenoxy.

"Aralkyl" means an alkyl group substituted by an aryl radical. The preferred aralkyl groups are benzyl or phenethyl.

The preferred aralkoxy groups are benzyloxy and phenethoxy.

"Halo" means a halogen. Preferred halogens include chloride, bromide and fluoride. The preferred haloalkyl group is trifluoromethyl.

This invention discloses mono- and bicyclic aryl ring compounds comprising two ring substituents, the first substituent comprising a lipophilic group and a terminal carboxylic acid or derivative group, and the second substituent comprising an amido group.

More specifically, the mono- and bicyclic aryl compounds are described by formula I:

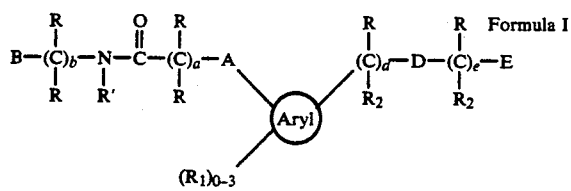

wherein:

Aryl is a mono- or bicyclic ring of about 5 to about 12 atoms which may be partially or completely unsaturated carbocyclic or heterocyclic where each ring of said monocyclic and bicyclic system contains 0-2 hetero atoms provided said hetero atoms are not vicinal oxygen and/or sulfur atoms;

R is independently hydrogen or $-(CH_2)_z-R_1$ where z is 0-5 or together with a vicinal R, R' or $R_2$ group forms a 4-7 membered ring;

$R_1$ is hydrogen, alkyl, alkenyl, alkoxy, amino, mono- and di-alkylamino, mercapto, alkylthio, nitro, halo or haloalkyl;

$R_2$ is independently H, R' or

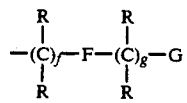

provided at least one of $R_2$ is other than H or R';

A is $-CRR$, O, S, NR', SO or $SO_2$;

B and G are each independently substituted or unsubstituted monocyclic or bicyclic aryl;

D O, S, $NR_2$, SO, $SO_2$, $CONR_2$, $NR_2CO$, $CRR_2$, $(CR_2=CR_2)_x$ where x is 0-2 or $C\equiv C$;

E is $-COOR'$, $-CONR'R'$,

where y is 2-5, $-CN$, $CONHSO_2R'$,

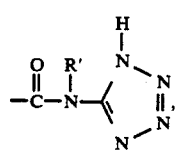

tetrazolyl or tetrazolyl substituted with alkyl, carboxyalkyl or carbalkoxyalkyl;

F is O, S, NR', SO, $SO_2$, CONR', NR'CO, CR'R', $(CR'=CR')_x$ where x is 0-2 or $C\equiv C$;

R' is hydrogen, alkyl or aralkyl;

a, b, d, e, f and g are independently 0-3 provided $a+b+d+e+f+g>1$, $a+b\neq 0$, $d+e+f+g>1$ and $d+f+g+x\neq 0$; or a pharmaceutically acceptable salt thereof.

Preferred monocyclic rings include pyrrole, thiophene, furan, cyclopentadiene, imidazole, pyrazole, 1,2,4-triazole, pyridine, pyrazine, pyrimidine, pyradazine, isothiazole, isoxazole, s-triazine and benzene.

Preferred bicyclic ring systems include indene, isoindene, benzofuran, benzothiophene, indole, 1H-indazole, indoline, benzopyrazole, benzoxazole, purine, naphthalene, tetralin, coumarin, chromone, quinoline, isoquinoline, quinazoline, pyrido[3,4-b]pyridine and 1,4-benzisoxazine.

The more preferred compounds of this invention include those of formulae II and III

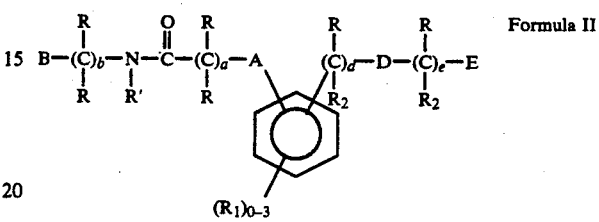

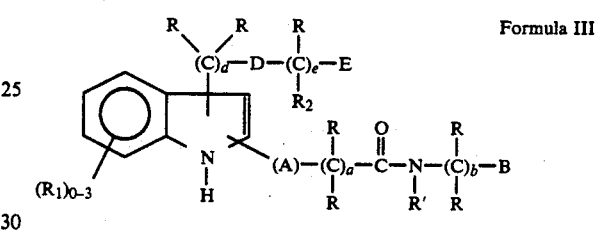

where:

A, B, D, E, R, R1, R2, R', a, b, d and e are as described above and the substituents of Formula III may be located at any appropriate position of either ring of the indole molecule.

A special embodiment of this invention may be described where A is $-(CH_2)_{0-4}-A'$ where A' is O or S, thus

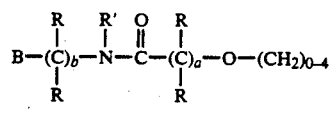

and

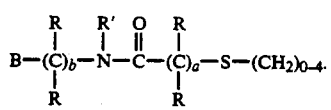

Turning now to the substituents which are necessarily a part of this invention and comprise three specific functional groups, the preferred first substituent, which we have called the amido function, may be described by formula IV:

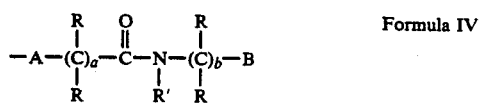

This is attached directly to the aryl ring.

The preferred second substituent having a terminal carboxylic acid or derivative thereof may be described by formula V:

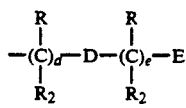
Formula V

This is also attached directly to the aryl ring.

The preferred third substituent, the lipophilic substituent, is also one of the definitions for $R_2$ and may be described by formula VI:

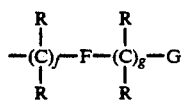
Formula VI

This is attached to the terminal carboxylic acid or derivative thereof substituent at a position on the acid substituent described by $R_2$.

Thus, for example, the lipophilic substituent of Formula VI can be combined with the terminal carboxylic acid or acid derivative function to obtain substituents 1-3 as follows:

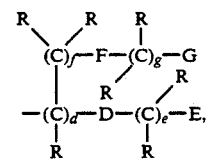 (1)

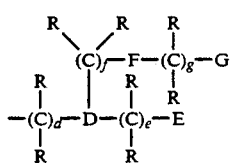 (2)

and

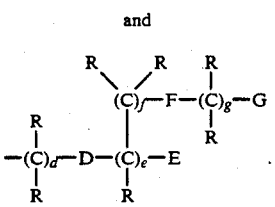 (3)

The remaining positions on the aryl ring, if available, may be substituted by $R_1$. In the case of those compounds having an available protonated nitrogen atom in the ring, this may be substituted by one of the above substituents or substituted by hydrogen or alkyl.

Even more preferred are those compounds described by Formulae IV, V and VI where:

A is CHR or O;

B and G are independently phenyl or substituted phenyl where the substituents are loweralkyl, loweralkoxy, carboxyloweralkyl or carbloweralkoxyloweralkoxy;

D is O, —$CHR_2$, $CONR_2$, $NR_2CO$, $(CR_2=CR)_x$ where x is 0-2 or C≡C;

E is —COOR' or tetrazolyl;

F is O, —CHR1, $CONR_4$, NR'CO, (CR'=CR') where x is 0-2 or C≡C;

R' is hydrogen, loweralkyl or arloweralkyl;

R is independently hydrogen or loweralkyl;

$R_1$ is hydrogen, loweralkyl or loweralkenyl;

$R_2$ is H, R' or

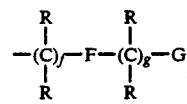

provided at least one of $R_2$ is other than H or R';

a, b, d, e, f and g are independently 0-3 provided a+b+d+e+f+g>1, a+b≠0, d+e+f+g>1 and d+f+g+x≠0.

Among the most preferred amido substituents are:

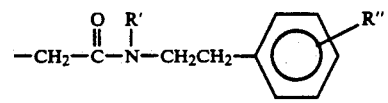

and

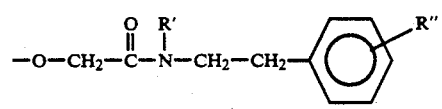

where R' is hydrogen or lower alkyl and R" is hydrogen, lower alkyl or lower alkoxy.

Among the most preferred terminal acidic substituents are: —$(CHR_2)_d$—E where d is 0-4, —$(CR_2=CR_2)_x$—E where x is 1-2, —O—$(CHR_2)_d$—E where d is 1-3, —O—$(CHR_2)_d$—$CR_2=CR_2$—E where d is 1-3 and $R_2$ is hydrogen, lower alkyl or the following most preferred lipophilic substituents; and E is —COOH or

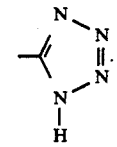

Among the most preferred lipophilic substituents are:

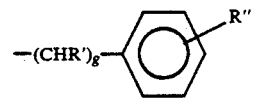

and

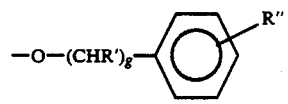

where g is 0-3 and R' is hydrogen or lower alkyl and R" is hydrogen, lower alkyl or lower alkoxy.

While this invention necessitates the presence of certain substituents attached to the aryl ring as described above, it is often desirable to have a third substituent present. This may be the same or different as those already present or it may also be derived from formulae IV to VI. Other substituents may likewise be desired as defined by $R_1$. It is to be understood that such compounds fall within the scope of this invention.

The preferred posistions for substitution in the molecule of formula II are the 1,3 and 1,4 positions.

The preferred positions for substitution in the compounds of formula III are the 1,3; 1,4 and 1,5 positions.

It may be of interest to one skilled in the art that compounds where E is OR' may also be of value as LTB$_4$ antagonists.

The compounds of this invention may be prepared by employing art recognized procedures from known compounds or readily preparable intermediates. Exemplary general procedures follow.

Since the compounds of this invention have certain substituents which are necessarily present on the aryl ring, the introduction of each substituent is, of course, dependent on the specific substituents involved and the chemistry necessary for their formation. Thus, consideration of how one substituent would be affected by a chemical reaction when forming a second substituent would involve techniques familiar to the skilled artisan. This would further be dependent on the ring involved.

It is convenient to synthesize these molecules by employing condensation reactions at reactive A, D and F cites of the molecule. Exemplary general procedures are as follows and are shown for convenience using the benzene and indole ring systems. Of course, while the following reactions involved are basic to developing substituted phenyl and indole molecules having the required substituents present, the substitution patterns for other mono- and bicyclic rings would depend on the chemistry of the particular ring. Any such adjustments to the chemistry would be familiar to one skilled in the art.

Thus, in order to prepare those compounds where A, D or F is O, S or NR' the following reactions or combination of reactions may be employed:

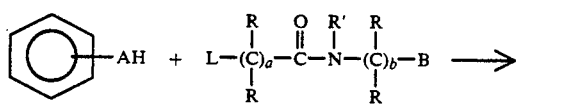

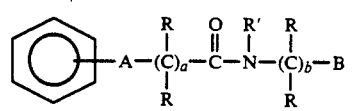

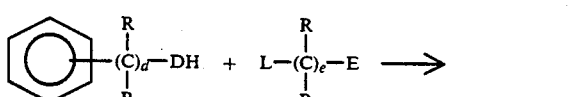

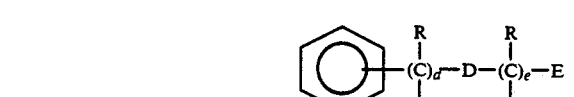

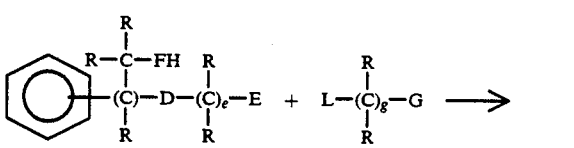

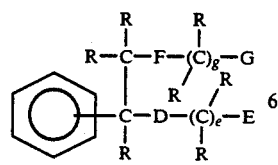

When A, D or F is O or S, the compounds may be prepared by condensation of the aryl alcohol or thiol with a compound of the formulae

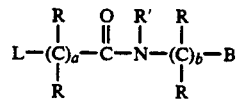

or

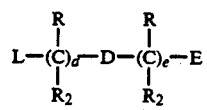

where E is preferably a nitrile, ester or tetrazole and L is a leaving group such as halo, tosylate or mesylate. This reaction is usually carried out in the presence of any base normally employed to deprotonate an alcohol or thiol such as sodium hydride, sodium hydroxide, triethyl amine, sodium bicarbonate, diisopropylethylamine or methyl magnesium halides.

Reaction temperatures are in the range of room temperature to reflux and reaction times may vary from 2 to 96 hours. The reaction is usually carried out in a solvent that will dissolve both reactants and is inert to both as well. Solvents include, but are not limited to diethyl ether, THF, N,N-dimethylformamide, dimethylsulfoxide, dioxane and the like.

When A is an alkyl group, it is convenient to prepare these compounds by Friedel-Crafts alkylation or by the Wittig reaction followed by reduction.

In the case where A, D or F is SO or SO$_2$, then treatment of the thio compound with m-chlorobenzoic acid or sodium periodate results in the sulfinyl compound. Preparation of the sulfonyl compound may be accomplished by known procedures such as dissolving the sulfinyl compound in acetic acid and treating With 30% H$_2$O$_2$.

Those compounds where F and/or D are

where x is 1 or 2, are prepared by reacting the appropriate aldehyde or ketone with an appropriate Wittig reagent or modified Wittig reagent of the formula

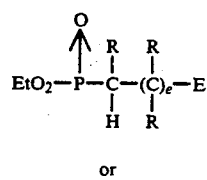

or

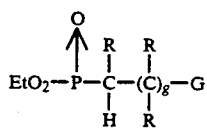

where E is cyano or carbalkoxy. Thus for example

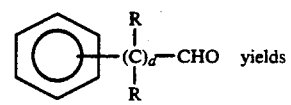

yields

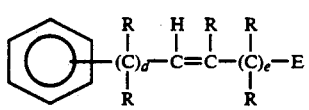

and

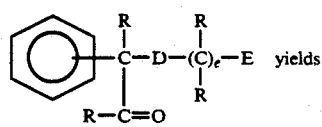

yields

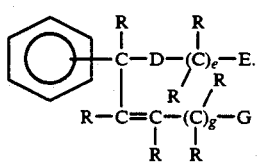

Reference for the Wittig reaction and modified Wittig reaction to control the formation of the trans and cis configuration at the double bond and the isomerization of cis and trans isomers can be found in A. Maercher, *Organic Reactions*, 14, 270, 1965.

The intermediate aldehyde compounds may be prepared in the usual manner from the corresponding carboxylic acid with an alkyllithium reagent, or from the oxidation of the corresponding alcohol. The aldehyde can also be obtained by Friedel-Crafts acylation or formylation (POCl$_3$/DMF) of the aryl ring.

When F and/or D are

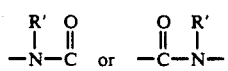

then the condensation of an acid or an acid halide with the appropriate aryl amine will give the desired compound.

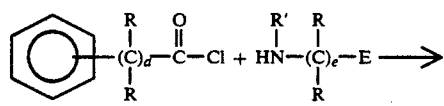

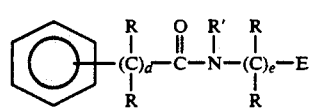

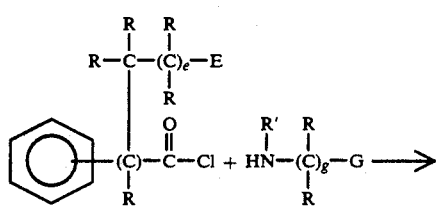

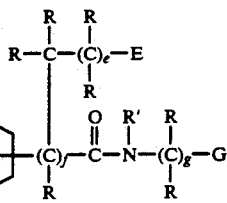

The tetrazoles may be formed from the nitrile at various stages of the synthesis by treatment with hydrazoic acid formed in situ from sodium azide and an acid. The nitrile may also be converted to the acids, esters or amides by known methods.

It is convenient to develop the synthesis of the final product by successively forming each desired substituent in turn. Thus in order to prepare a compound such as

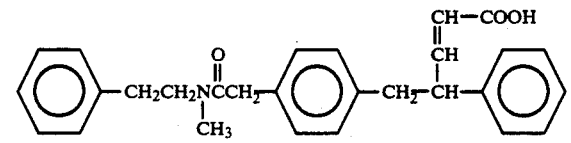

the following reaction sequence could be used:

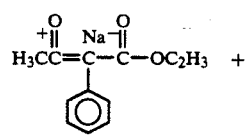

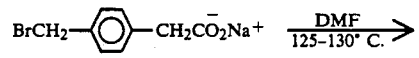

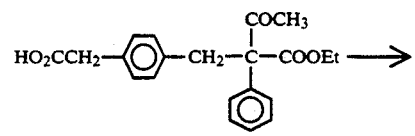

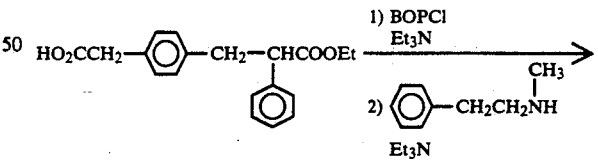

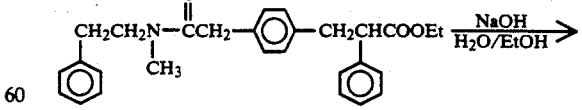

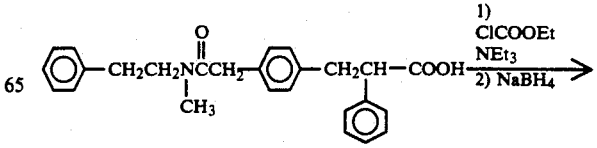

-continued
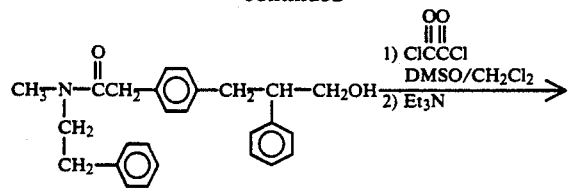
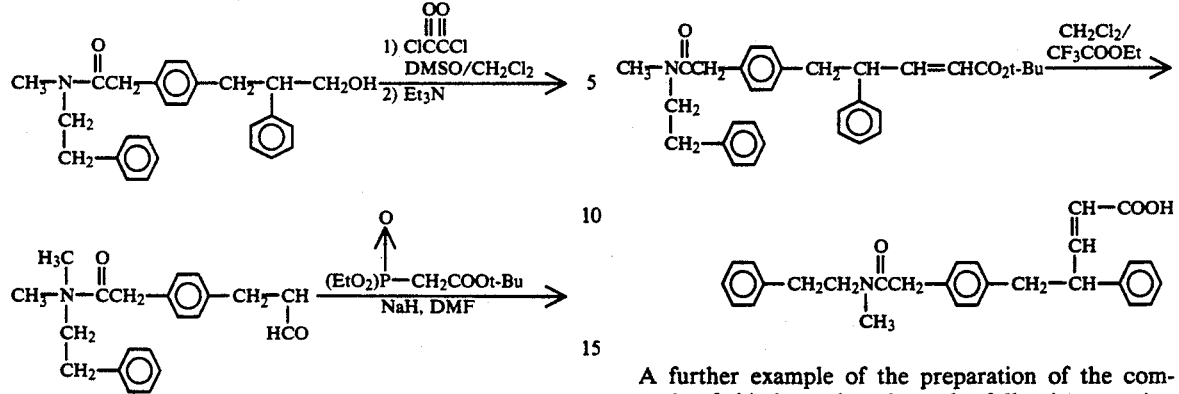
A further example of the preparation of the compounds of this invention show the following reaction synthesis to make
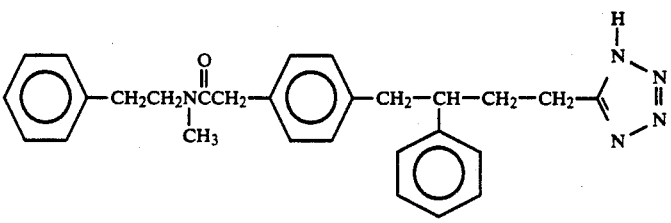
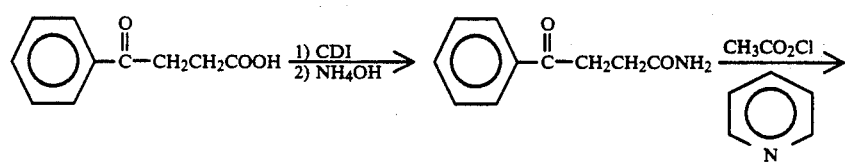
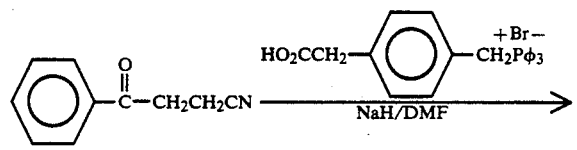
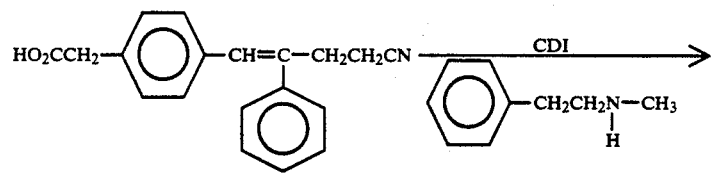
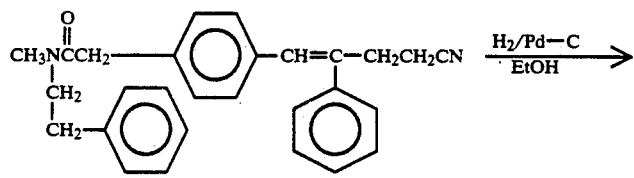
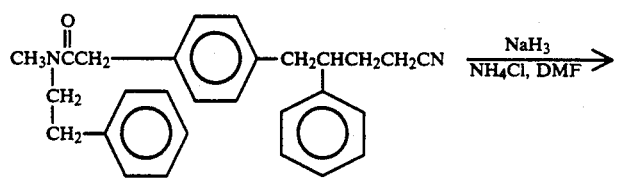

-continued

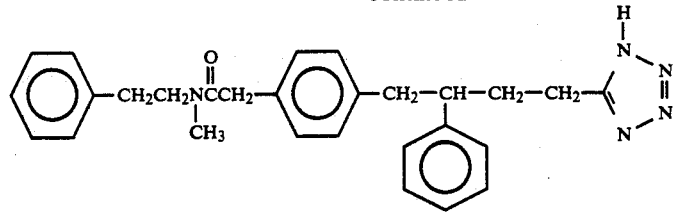

Certain compounds of this invention may have at least one asymmetric carbon atoms such as those compounds having different geminal R groups or those compounds Formulae V, VI and VIII which contain an asymmetric carbon atom. Further, certain compounds of this invention may exist in their cis or trans configuration such as those compounds where D is $CR_2=CR_2$ and F is $CR'=CR'$. As a result, those compounds of this invention may be obtained either as racemic mixtures, diastereoisomeric mixtures or as individual enantiomers. When two or three asymmetric centers are present the product may exist as mixtures of two or four diastereomers. Of course it is understood that certain other compounds within the scope of this invention could have a number of stereocenters. In general, a compound with x stereocenters can have a maximum of $2^x$ stereoisomers. Therefore, a compound having three such centers gives rise to a maximum of eight stereoisomers, while one having four produces sixteen, etc. The product may be synthesized as a mixture of the isomers and then the desired isomer separated by conventional techniques such as chromatography or fractional crystallization from which each diastereomer may be resolved. On the other hand, synthesis may be carried out by known stereospecific processes using the desired form of the intermediate which would result in obtaining the desired stereospecificity.

Reference to the separation of cis and trans isomers by chromatography may be found in W. K. Chan, et al. J. Am. Chem. Soc. 96. 3642, 1974.

It is to be understood that the scope of this invention encompasses not only the various isomers which may exist but also the various mixture of isomers which may be formed.

The resolution of the compounds of this invention and their starting materials may be carried out by known procedures. Incorporation by reference is hereby made to the four volume compendium *Optical Resolution Procedures for Chemical Compounds:* Optical Resolution Information Center, Manhattan College, Riverdale, N.Y. Such procedures are useful in the practive of this invention. A further useful reference is *Enantiomers, Racemates and Resolutions:* Jean Jacques, Andre Collet and Samuel H. Wilen; John Wiley & Sons, Inc., New York, 1981. Basically, the resolution of the compounds is based on the differences in the physical properties of diastereomers. Conversion of the racemates into a mixture of diastereomers by attachment of an enantiomerically pure moiety results in forms that are separable by fractional crystallization, distillation or chromatography.

The present compounds form salts with acids when a basic amino function is present and salts with bases when an acid function, i.e., carboxyl, is present. All such salts are useful in the isolation and/or purification of the new products. Of particular value are the pharmaceutically acceptable salts with both acids and bases. Suitable acids include, for example, hydrochloric, sulfuric, nitric, benzenesulfonic, toluenesulfonic, acetic, maleic, tartaric and the like which are pharmaceutically acceptable. Basic salts for pharmaceutical use are the Na, K, Ca and Mg salts.

Various substituents on the present new compounds, e.g., as defined in $R_1$ and $R''$ can be present in the starting compounds, added to any one of the intermediates or added after formation of the final products by known methods of substitution or conversion reactions. If the substituents themselves are reactive, then the substituents can themselves be protected according to the techniques known in the art. A variety of protecting groups known in the art, may be employed. Examples of many of these possible groups may be found in "Protective Groups in Organic Synthesis" by T. W. Green, John Wiley and Sons, 1981. For example, nitro groups can be added by nitration and the nitro group converted to other groups, such as amino by reduction, and halo by diazotization of the amino group and replacement of the diazo group. Acyl groups can be added by Friedel-Crafts acylation. The acyl groups can then by transformed to the corresponding alkyl groups by various methods, including the Wolff-Kishner reduction and Clemmenson reduction. Amino groups can be alkylated to form mono- and di-alkylamino groups; and mercapto and hydroxy groups can be alkylated to form corresponding ethers. Primary alcohols can be oxidized by oxidizing agents known in the art to form carboxylic acids or aldehydes, and secondary alcohols can be oxidized to form ketones. Thus, substitution or alteration reactions can be employed to provide a variety of substituents throughout the molecule of the starting material, intermediates, or the final product.

Compounds within the scope of the present invention have potent activity as leukotriene $B_4$ antagonists and as such possess therapeutic value in the treatment of inflammatory conditions and hypersensitivity responses. $LTB_4$ is implicated in diseases such as rheumatoid arthritis, gout, psoriasis and inflammatory bowel disease and therefore compounds which demonstrate $LTB_4$ antagonist properties would be of value in the control of these states.

The $LTB_4$ guinea pig polymorphonuclear membrane binding assay can be used to determine compounds exhibiting $LTB_4$ receptor antagonist properties. Compounds active in this assay can then be subjected to the guinea pig peritoneal PMN $LTB_4$-induced aggregation assay. THE $LTB_4$-induced aggregation assay determines the functional activity of a compound. The guinea pig $LTB_4$-induced wheal assay is used to determine in vitro activity.

ASSAY FOR INHIBITORS OF (³H)-LTB₄ BINDING TO MEMBRANES FROM GUINEA PIG POLYMORPHONUCLEAR LEUKOCYTES

Preparation of test compounds

Dissolve compounds to a concentration 100-fold higher than the highest desired concentration for testing. Serially dilute the compound so that all dilutions are 100-fold higher than the assay concentration desired. Compounds are typically dissolved in DMSO. If compounds are insoluble in DMSO, solutions are heated or sonicated to induce solubilization. Compounds may also be dissolved in ethanol.

Final assay concentrations of DMSO and ethanol can be as high as 1.0% and 2.0% (v/v); these concentrations have no measurable effects on specific binding.

Preparation of the membrane receptor fraction

To obtain polymorphonuclear leukocytes (PMNs), 25–30 male Hartley guinea pigs (250–350g) are intraperitoneally injected with 6 mls of an 8% sodium caseinate solution. 18 to 24 hours later, the guinea pigs are sacrificed by decapitation. The peritoneal cavity is lavaged with 15 mls of isolation buffer. The cells are collected and centrifuged at 200×g for 10 minutes. Contaminating red blood cells can be removed by hypotonic lysis. The cells are resuspended in isolation buffer and centrifuged as before. They are filtered through gauze and centrifuged again. The resulting pellet is suspended in 3 ml of sonication buffer, counted and brought to a concentration of $1 \times 10^8$ cells/ml. This suspension is lysed on ice with 5 bursts of 30 seconds separated by 1 minute intervals. The homogenate is centrifuged at 200×g for 10 minutes at 4° C. Aliquots of supernatant are transferred to high speed centrifuge tubes (1 tube per 3 guinea pigs). The tubes are centrifuged at 49,000×g for 15 minutes at 4° C. The pellets are resuspended by three 5 second bursts of sonication, separated by 20 second intervals. This suspension is centrifuged at 50,000×g for 20 minutes at 4° C. Pellets are stored at −70° C. for up to 3 months.

To use in the binding assay, the pellet is thawed at room temperature and suspended in 9 mls of assay buffer (sonication may be necessary).

Binding assay

Each assay tube (16×100 mm) contains the following:

345 μl Assay Buffer
5 μl Test compound or solvent
50 μl ³H-LTB₄ (0.50 nM)
100 μl Protein preparation (0.2 mg)

Incubations are done at 30° C. for 40 minutes in a water bath. Reactions are started by the addition of (³H)-LTB₄ solution. Samples are collected via a Brandel M24 Harvester for binding assays. Tubes should be washed with a total of 19 ml cold wash buffer.

The filters are transferred to 7 ml plastic scintillation vials to which 6.0 ml of appropriate scintillation fluid (e.g., Scintiverse ®) is added. After being allowed to equilibrate for 12 hours, the radioactivity is counted with a liquid scintillation counter appropriately set for tritium.

The required control assay tubes include the following:

(a) Total Binding: No test compound is added; buffer is substituted.

(b) Non-Specific Binding: Non-labeled ligand is added at a concentration of 1 μM.

(c) Solvent Controls: If test compound is dissolved in a solvent, controls for both Total Binding and Non-Specific Binding containing solvent but no compounds are required.

Calculations

Specific binding is defined as that amount of radioligand prevented from binding by 1000-fold excess non-labeled ligand, i.e., total binding minus non-specific binding. This operational definition is verified by Scatchard analysis of total binding.

Inhibition of specific binding is defined as the decrease in specific binding caused by the test compound, $$\frac{SB_C - SB_T}{SB_C} \times 100$$

where $SB_C$ is the specific binding in the absence of test compound and $SB_T$ is the specific binding in the presence of test compound. The $I_{50}$ values (concentrations required to inhibit specific binding by 50%) are determined by graphic analysis of the specific binding observed in the presence of various concentrations of test compound.

The results of this test indicate that compounds of this invention exhibit valuable LTB₄ receptor binding properties which are useful in the treatment of inflammatory conditions and hypersensitivity responses.

LTB₄-Induced Wheal Formation in Guinea Pig

LTB₄ plays the role of a mediator in cellular induced inflammation. The induction of chemokinesis and chemotaxis of PMNs and macrophage by LTB₄ have contributed to its association with the vascular aspects of acute inflammatory reactions.

In this test intradermal injection of 0.1 ml of a 10 μg/ml solution of LTB₄ to guinea pig back skin causes the formation of a wheal. This wheal is visualized by the prior intravenous injection with the indicator 1% Evan's Blue dye. Following a 2 hour incubation post-LTB₄ challenge, the guinea pigs are euthanized via CO₂ asphyxiation. Their dorsal skins are reflected and the diameters of the challenged sites are compared with those of the vehicle control injected sites.

Preparation and handling of guinea pig

The guinea pigs must be quarantined 5 to 7 days prior to the study. The day before the test, the back and hind limbs are shaved taking care not to nick the skin. After shaving, the guinea pigs are fasted, but water is provided.

On the day of the test, the guinea pigs are weighed and identified with an ink mark designating them with numbers 1 through 5 in each group. Groups are formed by random distribution.

Preparation and route of administration of compounds

The oral vehicles are Polyethylene Glycol (PEG 400) (2 ml/kg) and methocel (0.5% w/v) (10 ml/kg). Exposure to the ultrasound of a Branson sonicator assures uniformity of suspension or dissolution of the test compounds. Compounds for parenteral administration are dissolved in saline with the assistance of 0.1N HCl and 0.1N NaOH and then adjusting the pH to near neutrality.

Although test compounds are usually administered orally, other routes of administration such as intravenous, intraperitoneal or subcutaneous may be used.

Preparation of leukotriene B4 for intradermal injection

LTB$_4$ is obtained as a stock solution (50 µg/ml) in ethanol and is stored at $-80°$ C. until required for use. The stock solution or an appropriate aliquot is transferred from the ampule into a 10 ml glass vial using a pasteur pipette. The stock solution is then evaporated to dryness under a slow, steady stream of argon gas.

A solution of freshly prepared 0.25% Bovine Albumin in Phosphate-Buffered Saline is bubbled with argon gas until the saturation point is reached (approximately 5 minutes). This argon-saturated vehicle is then used to reconstitute the evaporated LTB$_4$ stock residue to yield a final working concentration of 10 µg/ml. The rubber stoppered vial of LTB$_4$ working solution is kept on wet ice during the study.

Preparation of Evan's Blue dye solution

Because Evan's Blue is an easily visible marker that binds to the plasma proteins, it has been selected to assist the investigator in the measurement of the wheals induced during the study. Evan's Blue Dye is dissolved as a 1% w/v solution in 0.9% w/v physiologic saline. The number of 1 ml plastic disposable syringes, fitted with 27 gauge, ½ inch needles and filled with the 1% dye solution, is determined by the number of animals expected to be included in the study.

Conduct of an experiment

Test compounds or their appropriate controls are administered orally with 16 gauge, 3 inch dosing cannulas. Immediately after dosing, the guinea pig is injected intravenously with 1 ml of 1% Evan's Blue Dye into a digital vein in the left or right shaved hind limb. This injection is facilitated best through the use of a 1 ml plastic syringe fitted with a 27 gauge, ½ inch needle. Immediately following Evan's Blue injection, the guinea pig is injected intracutaneously at each of 2 sites in the shaved dorsal midline with 0.1 ml of the prepared argon-saturated LTB$_4$ solution (1 µg/0.1 ml). A third site is intracutaneously injected with the argon-saturated 0.25% bovine albumin in phosphate-buffered saline to serve as a vehicle control.

2 hours after challenge, the guinea pigs are euthanized by inhalation of carbon dioxide. Carbon dioxide is administered by inserting a rubber tube from the tank into a plastic bag containing the caged group of guinea pigs. Asphyxiation occurs in approximately 5 minutes.

After death, the dorsal skins are reflected to enable the measurement of 2 perpendicular diameters of the resultant wheals. The area of each wheal is determined using the formula: Area$=\pi r^2$.

Calculations and statistics

For each guinea pig, the mean of the wheal areas obtained for the 2 injections sites is established after correction is made for the effect of the wheal area induced by the 0.25% Bovine Albumin in Phosphate-Buffered Saline vehicle. Then, a mean area for each treatment group with its corresponding standard error is calculated.

The following equation is used to calculate the percent inhibition of vehicle treated control wheal area by treatment with test compound:

$$\frac{\text{Mean Wheal Area}_{[Control]} - \text{Mean Wheal Area}_{[Treated]}}{\text{Mean Wheal Area}_{[Control]}}$$

In multiple dose experiments, the dose of a test compound that will cause 50% inhibition (ED$_{50}$) can be calculated from the regression equation for the response as percent inhibition (y) and log dose (x) and estimating the (ED$_{50}$) from: $_y(50) = bx + m$ where:

$\hat{y} = 50\%$ inhibition,
x = dose of test compound,
b = slope of dose response line and
m = intercept of the dose response line.

95% confidence limits of ED$_{50}$ are calculated from the regression equation by the method of Litchfield and Wilcoxon where:

$$ED_{25} = \hat{y}(25) = bx + m,$$
$$ED_{75} = \hat{y}(75) = bx + m \text{ and}$$
$$S = \frac{(ED_{75}/ED_{50}) + (ED_{50}/ED_{25})}{2}$$

where S is the slope function used to compute the limit factor fED$_{50}$ 2.77/$\sqrt{N}$ as fED$_{50}$=S. 2.77 is an estimator, N is the square root of the number of animals used for all the doses and fED$_{50}$ is the factor to determine the upper (RU) and lower (RL) limits of the ED$_{50}$ as: RU=ED$_{50}$×fED$_{50}$ and RL=ED$_{50}$+fED$_{50}$. Statistical significance of any inhibition caused by treatment with a test compound can be calculated by applying Student's t (two-tailed) to the data.

Validation and specificity studies

The 1 µg/0.1 ml/site challenge dose of LTB$_4$ was selected for the reproducibility, sensitivity and ease of measurement of the resultant wheal. Studies have indicated that size of wheals induced by LTB$_4$ is directly related to the dose administered.

2 hours of incubation after intradermal challenge with LTB$_4$ was selected as the routine timing for the study. Duration studies conducted evidenced the production of measurable, reproducible wheals at the 2 hour endpoint.

In view of the results obtained when compounds of the present invention are subjected to this test, it can be demonstrated that valuable properties as LTB$_4$ antagonists are indicated.

A further test which may be used to determine the ability of compounds of this invention to exhibit LTB: antagonist activities is as follows:

GUINEA PIG POLYMORPHONUCLEAR LEUKOCYTE AGGREGATION ASSAY

Isolation of guinea pig PMNs 6 ml of 6% Na-caseinate (in saline) is injected intraperitoneally into 2 male guinea pigs (250–300g) lightly anesthetized with CO$_2$ or ether. The following day (18–24 hours post injection) the animals are sacrificed by decapitation or CO$_2$ overdose according to the SOP for nonclinical laboratory study methods.

A midline section of abdominal skin is removed and 13 ml Hanks buffer (containing 500 µl 10 mM EDTA/500 ml Hanks) plus 2 ml 7% Na-citrate is injected into the peritoneal cavity. The guinea pig is rocked back and forth 5 times. A small incision is made on the left side of the midline of the abdominal wall (avoid cutting obvious blood vessels). Use a fire-polished pasteur pipette to transfer the buffer plus cells from the abdominal cavity to 2 washed Nalgene (Oak Ridge) centrifuge tubes (half of buffer and cells in each tube). The tubes are then filled to 50 ml with additional citrate-Hanks buffer and centrifuged at 4000 rpm for 10 minutes.

Each pellet is resuspended in 1 ml of citrate-Hanks and then diluted to 50 ml with the same buffer. The cells are incubated for 30 minutes at room temperature on a HemaTek aliquot mixer. The cells are filtered through 2 layers of gauze into 50 ml with plastic beakers to remove PMN aggregates and then transferred to fresh, washed, 50 ml Nalgene centrifuge tubes.

The cells are centrifuged for 5 minutes, resuspended in 50 ml of fresh buffer, centrifuged again and then resuspended in 3 ml of citrate-free Hanks buffer. (Following any centrifugation the cells are always resuspended first in 1 ml of the desired fresh buffer.)

An aliquot of the washed cells, diluted 50-fold, is counted using a microscope and a hemacytometer.

The PMNs are counted as follows:
1. Dilute 50 $\mu$l of cells into 450 $\mu$l of Hank's buffer.
2. Dilute 50 $\mu$l of (1) with 150 $\mu$l of Hank's buffer plus 50 $\mu$l of Toluidine blue (50× total dilution). Add 10 $\mu$l of (2) to the hemacytometer and count cells in 16 large squares (volume counted = 1 $\mu$l). View the hemacytometer under 40× magnification. The unstained cells are PMNs.

Calculation: assume 149 cells are counted.

$$\frac{\text{\# of cells counted/ml dilution factor} \times 2 \text{ ml}}{\text{desired final cell concentration}} = \text{Final volume of buffer needed/ml of cells}$$

cells/ml = 149/.0001 = 1,490,000 cells/ml $$\frac{1.49 \times 10^6 \times 50 \times 1}{3 \times 10^7} = \frac{7.45 \times 10^8}{3 \times 10^7} = 2.48 \text{ ml/ml of cells counted}$$

Thus, cells must be diluted 2.48-fold With Hanks buffer (2.48×3=7.44 ml; 7.44−3.0=4.44; add 4.44 ml buffer to the 3 ml of washed cells). This results in 7.44 ml of cells at a concentration of $3 \times 10^7$ cells per ml.

Instrument adjustments

Place cuvettes containing $1 \times 10^7$ cells/ml (166 $\mu$l PMNs plus 334 $\mu$l buffer) plus flea magnets in the aggregometer sample wells. Turn on the Chart Advance to 30 cm/hr. Turn the attenuation dials to mid range and decrease the recorder mV range settings to 50 mV full scale. Press the red "zero" button on the aggregometer and note exactly the position of the recorder pens. Turn the aggregometer left hand "PPP" dials for each cuvette position to the left or right so that the associated recorder pens move to the exact positions noted by pressing the red "zero" button. The electrical circuits are now "balanced". Except for small balance adjustments, do not make any further changes in pen positions by adjusting the "PPP" dials.

Withdraw one of the cuvettes from the aggregometer and note the (positive) direction of recorder pen motion. Replace the cuvette. Using the recorder zero knob, move the recorder pen in the positive direction to the chart paper 95% line. The pens now should not move when the red "zero" button is pressed. The pen also should not move when the mV sensitivity range is changed to 20 or 10 mV full scale (leave at 10 mV).

PMN aggregation should cause the pen to move in the "negative" direction across the chart paper. Make comparable adjustments for the second aggregometer channel but zero the recorder pen on the opposite side of the chart paper. Finally, pressing the zero button on either the recorder or the aggregometer should not cause the pens to move more than a mm or two. This instrument configuration will result in maximal pen deflection following aggregation of cells.

Aggregation studies

To a cuvette containing 334 $\mu$l of buffer and a flea magnet, add 166 $\mu$l of PMNs, 10 $\mu$l of $Ca^{++}/Mg^{++}$ (70/et mM; 1.4/0.7 mM final) and 5 $\mu$of 10 $\mu$M cytochalasin-$\beta$ allow to warm up in the aggregometer (37° C.) for 5 minutes and then add 1 $\mu$l of test compound in DMSO or DMSO carrier alone. Note compound effects, if any, for 2 minutes, then add 5 $\mu$l of the challenge agonist ($LTB_4$, PAF, etc.) and observe the response for at least 2 minutes. The standard concentrations of agonists used in this assay are arachidonic acid, 6 $\mu$M; $LTB_4$, 0.3 nM; PAF, 30 pM; and FMLP, 0.6 nM.

Aggregation is quantitated by measuring, in millimeters, the average maximum deflection of the pen line at 1 minute or less after the addition of $LTB_4$. The maximum response to a control challenge with arachidonic acid may develop somewhat more slowly than this.

Each aggregometer-recorder channel should include its own series of control aggregations. All compounds should be tested at least twice at each concentration of interest. The inhibitory activity observed is expressed as the mean percent change (inhibition) observed relative to the controls determined in that channel. Controls must include appropriate solvent blanks.

The results of the above test demonstrate that compounds within the scope of this invention inhibit the activity of $LTB_2$.

The compounds of the present invention can be administered to a mammalian host in a variety of forms adapted to the chosen route of administration, i.e., orally, or parenterally. Parenteral administration in this respect includes administration by the following routes: intravenous, intramuscular, subcutaneous, intraocular, intrasynovial, transepthelially including transdermal, ophthalmic, sublingual and buccal; topically including ophthalmic, dermal, ocular, rectal and nasal inhalation via insufflation and aerosol and rectal systemic.

The active compound may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipient and used in the form of ingestible tablets, buccal tablets, trochees, capsules, elixirs, suspensions, syrups, wafers, and the like. Such compositions and preparations should contain at least 0.1% of active compound. The percentage of the compositions and preparations may, of course, be varied and may conveniently be between about 2 to about 6% of the weight of the unit. The amount of active compound in such therapeutically useful compositions is such that a suitable dosage will be obtained.

Preferred compositions or preparations according to the present invention are prepared so that an oral dosage unit form contains between about 50 and 300 mg of active compound.

The tablets, trochees, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens a preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

The active compound may also be administered parenterally or intraperitoneally. Solutions of the active compound as a free base or pharmacologically acceptable salt can be prepared in water suitably mixed with a surfactant such as hydroxy-propylcellulose. Dispersion can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It may be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique which yield a powder of the active ingredient plus any additional desired ingredient from previously sterile-filtered solution thereof.

The therapeutic compounds of this invention may be administered to a mammal alone or in combination with pharmaceutically acceptable carriers, as noted above, the proportion of which is determined by the solubility and chemical nature of the compound, chosen route of administration and standard pharmaceutical practice.

The physician will determine the dosage of the present therapeutic agents which will be most suitable for prophylaxis or treatment and it will vary with the form of administration and the particular compound chosen, and also, it will vary with the particular patient under treatment. He will generally wish to initiate treatment with small dosages by small increments until the optimum effect under the circumstances is reached. The therapeutic dosage will generally be from 0.1 to 100 M/day or from about 0.1 mg to about 50 mg/kg of body weight per day and higher although it may be administered in several different dosage units. Higher dosages are required for oral administration.

The compounds of the present invention may be prepared by the following representative examples:

EXAMPLE 1

4-phenyl-5-[4-((N-methyl-N-phenethyl)carbamoylmethyl)phenyl]-E-pent-4-enoic acid 4-phenyl-5-[4-((N-methyl-N-phenethyl)carbamoylmethyl)phenyl]-Z-pent-4-enoic acid Step A: Methyl 4-phenyl-5-[(4-carboxymethyl)-phenyl]pent-4-enoate 4-(bromomethyl)phenylacetic acid (20g, 87.31 mmol) and triphenylphosphine (104.77 mmol, 27.48g) in toluene (240 ml) are heated at reflux for 18 hours. The reaction is filtered and air dried to give the triphenylphosphonium salt.

A mixture of this Wittig reagent (7.65g, 15.6 mmol) and NaH (60% suspension in mineral oil, 31.2 mmol, 1.25g of suspension) in DMF (25 ml) is stirred at 60° C. for 2 hours. Methyl 3-benzoylpropionate (3.0 g, 15.6 mmol) is added and the mixture stirred at 100°–110° C. for 24 hours. The reaction is poured into $H_2O$ (200 ml) and extracted with $Et_2O$ (3×100 ml). The water layer is then made acidic (concentrated HCl, pH~2) and the resulting suspension extracted with $Et_2O$ (3×300 ml). This $Et_2O$ layer is washed with $H_2O$ (5×100 ml) and dried ($MgSO_4$). Evaporation gives crude product. Chromatography of the residue with 5% MeOH in $CHCl_3$ on a 360 g silica gel column gives methyl 4-phenyl-5-[(4-carboxymethyl)phenyl]pent-4-enoate as a 5:1 mixture of E:Z isomers as determined by proton NMR.

Step B: Methyl 4-phenyl-5-[4-((N-methyl-N-phenethyl)carbamoylmethyl)phenyl]pent-4-enoate To a solution of 4-phenyl-5-[(4-carboxymethyl)-phenyl]pent-4-enoate (7.4g, 22.8 mmol) dissolved in THF (100 ml) is added 1,1'-carbonyldiimidazole (3.7 g, 22.8 mmol). The reaction is stirred at room temperature for 2 hours then N-methyl-N-phenethylamine (3.1 g, 22.8 mmol) is added and the reaction mixture is stirred at room temperature overnight. The reaction mixture is evaporated, partioned between $CH_2Cl_2$ and 1N HCl, then the CH$_2$Cl$_2$ layer is dried and evaporated to give methyl 4-phenyl-5-[4-((N-methyl-N-phenethyl)carbamoylmethyl)phenyl]pent-4-enoate. NMR confirms this product which is used directly in the next step.

Step C: 4-phenyl-5-4-((N-methyl-N-phenethyl)carbamoylmethyl)phenyl]-E-pent-4-enoic acid 4-phenyl-5-[4-((N-methyl-N-phenethyl)carbamoylmethyl)phenyl]-Z-pent-4-enoic acid The ester, methyl 4-phenyl-5-[4-((N-methyl-N-phenethyl)carbamoylmethyl)phenyl]pent-4-enoate, (3.9 g, 8.7 mmol) is stirred with LiOH.H$_2$O (1.9g, 44.1 mmol) in MeOH (90 ml) and H$_2$O (20 ml) at room temperature overnight. The MeOH is removed and then 1N HCl is added to the residue. The aqueous acid suspension is extracted with EtOAc (3×50 ml) and the organic layers dried (MgSO$_4$) and evaporated in vacuo. The resulting acid, a mixture of E:Z isomers (5:1 by proton NMR) is applied to a 200 g silica gel column and eluted with 1:1 petroleum ether:EtOAc. The first fractions of material eluted are pure 4-phenyl-5-[4-((N-methyl-N-phenethyl)carbamoylmethyl)phenyl]-Z-pent-4-enoic acid (0.15 g). The next fractions give a mixture of E:Z isomers of the acid followed by 4-phenyl-5-[4-((N-methyl-N-phenethyl)carbamoylmethyl)phenyl]-E-pent-4-enoic acid (0.22 g). The isomers are confirmed by NMR.

|   | cis | | trans |
|---|---|---|---|
|   | Calc'd | Found | Found |
| C | 78.66 | 77.11 | 78.94 |
| H | 6.84 | 6.76 | 7.14 |
| N | 3.28 | 3.12 | 3.66 |

EXAMPLE 2

4-phenyl-5-[4-((N-methyl-N-phenethyl)carbamoylmethyl)phenyl]pentanoic acid 4-phenyl-5-[4-((B-methyl-N-phenethyl)carbamoylmethyl)phenyl]pent-4-enoic acid (2.0 g) is dissolved in EtOH (50 ml) and shaken under 50 psi of H$_2$ in the presence of 10% Pd-C (200 mg) for 18 hours. The mixture is purged with N$_2$ then filtered (Celite) and evaporated in vacuo to give 4-phenyl-5-[4-((N-methyl-N-phenethyl)carbamoylmethyl)phenyl]pentanoic acid which is confirmed by NMR.

|   | Calc'd | Found |
|---|---|---|
| C | 78.24 | 75.54 |
| H | 7.27 | 6.71 |
| N | 3.26 | 3.04 |

EXAMPLE 3

5-[4-((4-(N-methyl-N-phenethyl)carbamoylmethyl)phenyl)-3-phenylbutyl]-1H-tetrazole Step A: 1-(4-carboxymethyl)phenyl-2-phenyl-4-cyanobut-1-ene When 3-benzoylpropionate in Example 1, Step is replaced by 3-benzoylethylnitrile then the product prepared is 1-(4-carboxymethyl)phenyl-2-phenyl-4-cyanobut-1-ene. This structure is confirmed by NMR and used directly in the next step.

Step B: 1-4-((N-methyl-N-phenethyl)carbamoylmethyl)phenyl]-2-phenyl-4-cyanobut-1-ene When the nitrile of Step A is used following the procedure of Example 1, Step B, then the product prepared is 1-[4-((N-methyl-N-phenethyl)carbamoylmethyl)phenyl]-2-phenyl-4-cyanobut-1-ene. This structure is confirmed by NMR and used directly in the next step.

Step C: 1-4-((N-methyl-N-phenethyl)carbamoylmethyl)phenyl]-2-phenyl-4-cyanobutane When the product of Step B is used following the procedure of Example 2, then the product prepared is 1-[4-((N-methyl-N-phenethyl)carbamoylmethyl)phenyl]-2-phenyl-4-cyanobutane. This structure is confirmed by NMR and used directly in the next step.

Step D: 5-[4-((4-(N-methyl-N-phenethyl)carbamoylmethyl)phenyl)-3-phenylbutyl-1H-tetrazole A mixture of 1-[4-(N-methyl-N-phenethyl)carbamoylmethylphenyl]-2-phenyl-4-cyanobutane (0.82 g, 2 mmol), NaN$_3$ (1.2 g, 18 mmol), NH$_4$Cl (0.96 g, 18 mmol) and DMF (5 ml) is heated to 100° C. for 10 hours. This is then poured in H$_2$O and extracted with ethyl acetate (2×25 ml). The ethyl acetate is dried (Na$_2$SO$_4$) and concentrated in vacuo. The oily residue is chromatographed used 1:1 hexane/EtOAc until all starting material (nitrile) is removed (TLC). The solvent is changed to ethyl acetate and the material collected to obtain 5-[4-((4-(N-methyl-N-phenethyl)carbamoylmethyl)phenyl)-3-phenylbutyl]-1H-tetrazole. NMR confirms this structure.

|   | Calc'd | Found |
|---|---|---|
| C | 74.14 | 69.25 |
| H | 6.89 | 6.76 |
| N | 15.44 | 14.80 |

EXAMPLE 4

4-phenyl-5-[4-((N-methyl-N-phenprop-2-yl)-carbamoylmethyl)phenyl]pentanoic acid

Step A: Methyl 4-phenyl-5-[4-((N-methyl-N-phenprop-2-yl)carbamoylmethyl)phenyl]pent-4-enoate When N-methyl-N-phenethylamine of Example 1, Step A is replaced with N-methyl-N-phenprop-2-ylamine then the product prepared is methyl 4-phenyl-5-[4-((N-methyl-N-phenprop-2-yl)carbamoylmethyl)phenyl]pent-4-enoate. This is confirmed by NMR and used directly in the next step.

Step B: Methyl 4-phenyl-5-4-((N-methyl-N-phenprop-2-yl)carbamoylmethyl)phenyl]pentanoate When the ester from Step A is hydrogenated following the procedure of Example 2, then the product prepared is Methyl 4-phenyl-5-[4-((N-methyl-N-phenprop-2-yl)carbamoylmethyl)phenyl]pentanoate. This is confirmed by NMR and used directly in the next step.

Step C: 4-phenyl-5-[4-((N-methyl-N-phenprop-2-yl)carbamoylmethyl)phenyl]pentanoic acid When the ester from Step B is hydrolyzed following the procedure of Example 1, Step C, then the product prepared is 4-phenyl-5-[4-((N-methyl-N-phenprop-2-yl)-carbamoylmethyl)phenyl]pentanoic acid.

|   | Calc'd | Found |
|---|---|---|
| C | 78.52 | 75.75 |
| H | 7.50 | 7.43 |
| N | 3.16 | 2.75 |

EXAMPLE 5

4-phenyl-5-[4-((N-methyl-N-phenprop-2-yl)carbamoyl-methyl)phenyl]-E-pent-4-enoic acid 4-phenyl-5-[4-((N-methyl-N-phenprop-2-yl)carbamoylmethyl)phenyl]-Z-pent-4-enoic acid When methyl 4-phenyl-5-[4-((N-methyl-N-phenethyl)carbamoylmethyl)phenyl]pent-4-enoate of Example 1, Step C is replaced with 4-phenyl-5-[4-((N-methyl-N-phenprop-2-yl)carbamoyl)phenyl]pent-4-enoate then the cis and trans products are prepared. NMR confirms these structures.

EXAMPLE 6

When N-methyl-N-phenprop-2-ylamine of Example 4, Step A is replaced with N-methyl-N-benzylamine, N-methyl-N-phenpropylamine and N-propyl-N-phenethylamine then the products prepared through Step C are: 4-phenyl-5-[4-((N-methyl-N-benzyl)carbamoylmethyl)phenyl]-pentanoic acid;

|   | Calc'd | Found |
|---|--------|-------|
| C | 78.04  | 75.81 |
| H | 7.03   | 7.29  |
| N | 3.37   | 3.19  |

4-phenyl-5-[4-((N-methyl-N-phenpropyl)carbamoylmethyl)phenyl]pentanoic acid; and

|   | Calc'd | Found |
|---|--------|-------|
| C | 78.52  | 75.64 |
| H | 7.50   | 7.46  |
| N | 3.16   | 2.86  |

4-phenyl-5-[4-((N-propyl-N-phenethyl)carbamoylmethyl)phenyl]pentanoic acid.

|   | Calc'd | Found |
|---|--------|-------|
| C | 78.74  | 78.44 |
| H | 7.71   | 7.77  |
| N | 3.06   | 2.85  |

EXAMPLE 7

2-phenyl-3-4-((N-methyl-N-phenethyl)carbamoylmethyl)phenyl]propanoic acid 4-phenyl-5-[4-((N-methyl-N-phenethyl)carbamoylmethyl)phenyl]pent-2-enoic acid Step A: 4-(2-phenyl-3-carbethoxypropyl)phenylacetic acid 4-(bromomethyl)phenylacetic acid (5.127 g, 22.38 mmol) is treated with NaH (22.38 mmol, 60% dispersion, 895 mg) and THF (20 ml). This is then evaporated to an oil and dissolved in dry DMF (25 ml) and transferred to a flask containing [the sodium salt of 2-carboethoxyphenylacetic acid (22.38 mmol, 4.61 g); 8.95 mg of 60% dispersion of NaOH in THF and then evaporated to a solid]. This is then heated at 130° C. for ¾ hours. The reaction mixture is poured into 1N HCl (250 ml) and extracted with EtOAc (250 ml) then washed with H₂O (5×100 ml), dried (MgSO₄) and evaporated.

4 equivalents (2.06 g, 88 mmol) of Na is reacted in EtOH (100 ml) to form a solution of NaOET/EtOH. This is cooled to 0° C. and 7.817 g of the above alkylated product in EtOH (30 ml) is added dropwise at 0° C. This is allowed to stir at room temperature overnight. To this mixture is then added 100 ml of 1N HCl followed by 500 ml of H₂O (pH about 3-4). The aqueous suspension is extracted with Et₂O (3×250 ml) and evaporated to dryness to obtain 4-(2-phenyl-3-carbethoxypropyl)phenylacetic acid which is confirmed by NMR and used directly in the next step.

Step B: Ethyl 2-phenyl-3-[4-((N-methyl-N-phenethyl)carbamoylmethyl)phenyl]propanoate To 3.96 g (12.65 mmol) of 4-(2-phenyl-3-carbethoxypropyl)phenylacetic acid in CH₂Cl₂ (100 ml) and triethylamine (1.2 equivalent, 2.12 ml) at −15° C. is added BOP·Cl (1.2 equivalent, 3.87 g). The reaction mixture is stirred at −15° C. for 20 minutes. To this is added dropwise N-methyl-N-phenethylamine (1.1 equivalent, 1.89 g) and triethylamine (1.2 equivalent, 2.12 ml) in CH₂Cl₂ (10 ml) at 0° C. The reaction was gradually allowed to warm to room temperature and stirred overnight. This was then evaporated to dryness in vacuo and then redissolved in EtOAC (300 ml), washed with 1N HCl (3×100 ml) and saturated NaHCO₃ (3×100 ml), dried (MgSO₄) and evaporated to dryness to obtain Ethyl 2-phenyl-3-[4-((N-methyl-N-phenethyl)carbamoylmethyl)phenyl]propanoate. This is purified by column chromatography using silica gel column (360 g) with 1:1/pet.ether:EtOAc to obtain product which is confirmed by NMR and IR and used directly in the next step.

Step C:
2-phenyl-3-[4-((N-methyl-N-phenethyl)carbamoylmethyl)phenyl]propanoic acid A mixture of ethyl 2-phenyl-3-[4-((N-methyl-N-phenethyl)carbamoylmethyl)phenyl]propanoate (6.59 g, 15.4 mmol) in EtOH (60 ml) and 2N NaOH (31 mmol, 15.5 ml) is heated at reflux for 3 hours. This is then evaporated to dryness and the residue partioned between 1N HCl and EtOAc. The organic layer is then washed with H₂O, dried and evaporated to dryness in vacuo to obtain 2-phenyl-3-[4-((N-methyl-N-phenethyl)carbamoyl-methyl)phenyl]propanoic acid which is confirmed by NMR and used directly in the next step.

|   | Calc'd | Found |
|---|--------|-------|
| C | 77.78  | 76.84 |
| H | 6.78   | 6.79  |
| N | 3.49   | 3.78  |

Step D: 2-phenyl-3-4-((N-methyl-N-phenethyl)carbamoylmethyl)phenyl]propanol

A solution of 2-phenyl-3-[4-((N-methyl-N-phenethyl)carbamoylmethyl)phenyl]propanoic acid (524 mg, 1.31 mmol) in THF 10 ml) is cooled to 0° C. To this is added triethylamine (0.13 ml, 1.31 mmol) and ethyl chloroformate (1.31 mmol, 0.13 ml). The reaction is allowed to stir at 0° for 30 minutes. This is then filtered into NaBH: (2 equivalent, 2.3 mmol, 150 mg) in H₂O 10 ml) and stirred for 3 hours. After this time it is diluted with 1N HCl then extracted with CH₂Cl₂, dried (MgSO₄) and evaporated in vacuo to obtain 2-phenyl-3-[4-((N-methyl-N-phenethyl)carbamoylmethyl)phenyl]-propanol which is confirmed by IR and NMR and used directly in the next step.

Step E: 1-[4-((N-methyl-N-phenethyl)carbamoyl)-phenyl]-2-formyl-2-phenylethane

To oxalyl chloride (12.52 mmol, 0.98 ml) in CH₂Cl₂ (30 ml) at −60° C. is added dropwise DMSO (27.35 mmol, 1.93 ml). The reaction mixture is stirred at −60° C. for 10 minutes. To this is added dropwise 2-phenyl-3-[4-((N-methyl-N-phenethyl)carbamoylmethyl)phenyl]-propanol (4.43 g, 11.45 mmol) in CH$_2$Cl$_2$ (10 ml). The reaction is stirred for 20 minutes then triethylamine (56.8 mmol, 7.9 ml) is added dropwise over 5 minutes. The reaction mixture is allowed to warm to room temperature and water (40 ml) is added. The reaction mixture is then stirred at room temperature for 15 minutes. Et$_2$O is added followed by water and the organic layer is partitioned. The organic layer is then extracted with 1N HCl (2×50 ml), H$_2$O (3×40 ml), dried (MgSO$_4$) and evaporated in vacuo to obtain 1-[4-((N-methyl-N-phenethyl)carbamoyl)phenyl]-2-formyl-2-phenylethane which is confirmed by NMR and used directly in the next step.

Step F: t-butyl 4-phenyl-5-[4-( N-methyl-N-phenethyl)carbamoylmethyl)phenyl]pent-2-enoate NaH (60% dispersion in mineral oil, 6.55 ml, 262 mg) is added to a cooled (0° C.) DMF (5 ml) solution of t-butyl acetate Horner-Emmons reagent (6.55 mmol, 1.65 g). When gas evaluation ceases 1-[4-((N-methyl-N-phenethyl)carbamoyl)phenyl]-2-formyl-2-phenylethane (1.94 g, 5.03 mmol) in DMF (10 ml) is added. The reaction mixture is then allowed to warm to room temperature with stirring. This is then diluted with H$_2$O, extracted with EtOAc (2×15 ml), dried (MgSO$_4$) and evaporated in vacuo to obtain t-butyl 4-phenyl-5-[4-((N-methyl-N-phenethyl)carbamoylmethyl)phenyl]pent-2-enoate. This is confirmed by NMR, purified by column chromatography using silica gel (360 g) and eluted with 2:1/EtOAc:petroleum ether. The product obtained is used directly in the next step.

Step G: 4-phenyl 5-[4-((N-methyl-N-phenethyl)carbamoylmethyl)phenyl]pent-2-enoic acid To t-butyl 4-phenyl-5-[4-((N-methyl-N-phenethyl)carbamoylmethyl)phenyl]pent-2-enoate (1.074 g, 2.22 mmol) in CH$_2$Cl$_2$ (20 ml) cooled to 0° C. is added trifluoroacetate acid (5 ml). The reaction mixture is allowed to warm to room temperature and stirred for 1 hour. This is diluted with CHCl$_3$ and evaporated to dryness several times to remove any trace of trifluoroacetic acid. This is then evaporated in vacuo to obtain 4-phenyl-5-[4-((N-methyl-N-phenethyl)carbamoylmethyl)phenyl]pent-2-enoic acid which is confirmed by NMR and purified by column chromatography using silica gel and eluted with 5% MeOH in CHCl$_3$.

|   | Calc'd | Found |
|---|--------|-------|
| C | 78.66  | 76.62 |
| H | 6.84   | 6.84  |
| N | 3.28   | 3.66  |

EXAMPLE 8

4-phenyl-5-4-((N-methyl-N-phenethyl)carbamoylmethyl)phenyl]pentanoic acid

With the product of Example 7, Step G is used following the procedure of Example 2, then the product prepared is 4-phenyl-5-[4-((N-methyl-N-phenethyl)carbamoylmethyl)phenyl]pentanoic acid. This structure is confirmed by NMR.

EXAMPLE 9

6-phenyl-7-[4-((N-methyl-N-phenethyl)carbamoylmethyl)phenyl]hept-2-enoic acid 6-phenyl-7-[4-((N-methyl-N-phenethyl)carbamoylmethyl)phenyl]heptanoic acid Step A: 4-phenyl-5-4-((N-methyl-N-phenethyl)carbamoylmethyl)phenyl]pentanol A mixture of 4-phenyl-5-[4-((N-methyl-N-phenethyl)carbamoylmethyl)phenyl]pentanoic acid (1.21 g, 2.82 mmol) in THF (20 ml) is cooled to 0° C. Triethylamine (0.39 ml, 2.82 mmol) is added followed by ethyl chloroformate (0.28 ml, 2.82 mmol). The reaction mixture is stirred at 0° C. for 3 hours, filtered into 2 equivalent of NaBH$_4$ (215 mg, 5.64 mmol) in H$_2$O (20 ml) at 0 C. This is stirred at 0° C., poured into 1N HCl, extracted with EtOAc, dried (MgSO$_4$) and evaporated to dryness to obtain 3-phenyl-4-[4-((N-methyl-N-phenethyl)carbamoylmethyl)phenyl]butane which is confirmed by NMR and IR and used directly in the next step.

Step B: 4-phenyl-5-[4-((N-methyl-N-phenethyl)carbamoylmethyl)phenyl]pentanal

When the procedure of Examle 7, Step E is followed and 2-phenyl-3-[4-((N-methyl-N-phenethyl)carbamoylmethyl)phenyl]propanol is replaced by 4-phenyl-5-[4-((N-methyl-N-phenethyl)carbamoylmethyl)phenyl]-pentanol then the product prepared is 4-phenyl-5-[4-((N-methyl-N-phenethyl)carbamoylmethyl)phenyl]-pentanal. This is confirmed by NMR and used directly in the next step.

Step C: Methyl 6-phenyl-5-[4((N-methyl-N-phenethyl)carbamoylmethyl)phenyl]hept-2-enoate When the procedure of Example 7, Step F is followed and 4-phenyl-5-[4-((N-methyl-N-phenethyl)carbamoylmethyl)phenyl]pentanal is used in place of 1-[4-((N-methyl-N-phenethyl)carbamoyl)phenyl]-2-formyl-2-phenylethane and the methyl acetate Wittig reagent is used then the product prepared is methyl 6-phenyl-5-[4-((N-methyl-N-phenethyl)carbamoylmethyl)phenyl]-hept-2-enoate. This is confirmed by NMR and IR and used directly in the next step.

Step D: 6-phenyl-5-4-((N-methyl-N-phenethyl)carbamoylmethyl)phenyl]hept-2-enoic acid To methyl 6-phenyl-5-[4-((N-methyl-N-phenethyl)-carbamoylmethyl)phenyl]hept-2-enoate (0.77 g, 1.65 mmol) in methanol (15 ml) is added with stirring Li-OH.H$_2$O (3 equivalent, 4.95 mmol, 210 mg) and H$_2$O (1 ml). The reaction mixture is stirred overnight, diluted with EtOAc (100 ml) washed with 1N HCl (50 ml), brine (50 ml), dried (MgSO$_4$) and evaporated to dryness to obtain 6-phenyl-5-[4-((N-methyl-N-phenethyl)carbamoylmethyl)phenyl]hept-2-enoic acid which is purified by column chromatography using silica gel (360 g) and eluted with 2% MeOH in CHCl$_3$. This structure is confirmed by NMR and IR.

|   | Calc'd | Found |
|---|--------|-------|
| C | 79.09  | 78.43 |
| H | 7.30   | 7.47  |
| N | 3.07   | 2.83  |

Step E: 6-phenyl-5-[4-((N-methyl-N-phenethyl)carbamoylmethyl)phenyl]heptanoic acid A solution of 6-phenyl-5-[4-((N-methyl-N-phenethyl)carbamoylmethyl)phenyl]hept-2-enoic acid (183 mg) in EtOH (25 ml) is shaken with 100 mg of 10%

Pd-C catalyst under 50 psi of $H_2$ overnight at room temperature. The reaction mixture is then filtered through celite and evaporated to dryness to obtain 6-phenyl-5-[4-((N-methyl-N-phenethyl)carbamoylmethyl)phenyl]heptanoic acid. This is confirmed by NMR and IR.

|   | Calc'd | Found |
|---|--------|-------|
| C | 78.74  | 74.64 |
| H | 7.74   | 7.66  |
| N | 3.06   | 2.65  |

EXAMPLE 10

2-methyl-4-phenyl-5-[4-((N-methyl-N-phenethyl)carbamoylmethyl)phenyl]pentanoic acid 2-methyl-4-phenyl-5-4-((N-methyl-N-phenethyl)carbamoylmethyl)phenyl]pent-2-enoic acid Step A: Ethyl 2-methyl-4-phenyl-5-4-((N-methyl-N-phenethyl)carbamoylmethyl)phenyl]pent-2-enoate When the procedure of Example 7, Step F is followed and the ethyl 2-methylacetate Wittig reagent is used, then the product prepared is ethyl 2-methyl-4-phenyl-5-[4-((N-methyl-N-phenethyl)carbamoylmethyl)phenyl]pent-2-enoate. This is confirmed by NMR, IR and used directly in the next step.

Step B: 2-methyl-4-phenyl-5-4-((-N-methyl-N-phenethyl)carbamoylmethyl)phenyl]pent-2-enoic acid A mixture of ethyl 2-methyl-4-phenyl-5-[4-((N-methyl-N-phenethyl)carbamoylmethyl)phenyl]pent-2-enoate (1.72 g) in EtOH (20 ml) is stirred with 3 equivalents of 2N NaOH (5.5 ml) at room temperature for 72 hours. This is then refluxed for 1 hour, filtered and evaporated to dryness. To this residue is then added 1N HCl (50 ml) and the reaction mixture extracted with EtOAc, dried (MgSO4) and evaporated in vacuo to obtain 2-methyl-4-phenyl-5-[4-((N-methyl-N-phenethyl)carbamoylmethyl)phenyl]pent-2-enoic acid. This is purified on column chromatography using silica gel (360 g) with 2:1/petroleum ether:EtOAc and then 1:1/petroleum ether:EtOAc where the latter gives pure product (m.p. 40°–50° C.) which is confirmed by IR, mass spec. and Hi-field NMR.

|   | Calc'd | Found |
|---|--------|-------|
| C | 78.88  | 77.99 |
| H | 7.08   | 7.27  |
| N | 3.17   | 3.13  |

Step C: 2-methyl-4-phenyl-5-[4-((N-methyl-N-phenethyl)carbamoylmethyl)phenyl]pentanoic acid Following the procedure of Example 2, and replacing 4-phenyl-5-[4-((N-methyl-N-phenethyl)carbamoylmethyl)phenyl]pent-4-enoic acid with 2-methyl-4-phenyl-5-[4-((N-methyl-N-phenethyl)carbamoylmethyl)-phenyl]pent-2-enoic acid the product prepared is 2-methyl-4-phenyl-5-[4-((N-methyl-N-phenethyl)carbamoylmethyl)phenyl]pentanoic acid (m.p. 43°–47° C.). This is confirmed by NMR, mass spec. and IR.

|   | Calc'd | Found |
|---|--------|-------|
| C | 78.52  | 76.96 |
| H | 7.50   | 7.57  |
| N | 3.16   | 3.09  |

EXAMPLE 11

4-phenyl-5-[3-((N-methyl-N-phenethyl)carbamoylmethyl)phenyl]pentanoic acid

Step A: Methyl 4-phenyl-5-[(3-carboxymethyl)-phenyl]pent-4-enoate

When the procedure of Example 1, Step A is followed and 3-(bromomethyl)phenylacetic acid is used in place of 4-(bromomethyl)phenylacetic acid then the product prepared is methyl 4-phenyl-5-[(3-carboxymethyl)phenyl]pent-4-enoate which is confirmed by NMR and IR and used directly in the next step.

Step B: 4-phenyl-5-[3-(carboxymethyl)phenyl]pentanoic acid

When the procedure of Example 2 is followed and the product from Step A is used in place of 4-phenyl-5-[4-((N-methyl-N-phenethyl)carbamoylmethyl)phenyl]-pent-4-enoic acid then the product prepared is 4-phenyl-5-[3-(carboxymethyl)phenyl]pentanoic acid which is confirmed by NMR and used directly in the next step.

Step C: Methyl 4-phenyl-5-[3-((N-methyl-N-phenethyl)carbamoylmethyl)phenyl]pentanoate When the procedure of Example 1, Step B is followed and 4-phenyl-5-[3-(carboxymethyl)phenyl]pentanoic acid is used in place of methyl 4-phenyl-5-[(4-carboxymethyl)phenyl]pent-4-enoate then the product prepared is methyl 4-phenyl-5-[3-((N-methyl-N-phenethyl)carbamoylmethyl)phenyl]pentanoate which is confirmed by NMR and IR and purified by column chromatography using silica and eluted with 3% EtOH in $CHCl_3$. This is used directly in the next step.

Step D: 4-phenyl-5-3-((N-methyl-N-phenethyl)carbamoylmethyl)phenyl]pentanoic acid When the procedure of Example 1, Step C is followed and the ester from Step C is used in place of methyl 4-phenyl-5-[4-((N-methyl-N-phenethyl)carbamoylmethyl)phenyl]pent-4-enoate then the product prepared is 4-phenyl-5-[3-((N-methyl-N-phenethyl)carbamoylmethyl)phenyl]pentanoic acid. This is confirmed by NMR and IR.

EXAMPLE 12

N-carboxymethyl 2-phenyl-3-[4-((N-methyl-N-phenethyl)carbamoylmethyl)phenyl]propanamide Step A: N-carbomethoxymethyl 2-phenyl-3-[4-((N-methyl-N-phenethyl)carbamoylmethyl)phenyl]-propanamide A mixture of 2-phenyl-3-[4-((N-methyl-N-phenethyl)carbamoylmethyl)phenyl]propanoic acid (2.09 g, 5.22 mmol), 1-(3-dimethylaminopropyl)-3-ethylcarbodiimide·HCl (5.22 mmol, 1.00 g), 1-hydroxybenzotriazole (5.22 mmol, 0.71 g), triethylamine (10.44 mmol, 1.056 g) and methylglycine·HCl (5.22 mmol, 0.655 g) are stirred at room temperature in $CH_2Cl_2$ (50 ml) for 72 hours. The reaction mixture is diluted with EtOAc (250 ml) and washed with 1N HCl (2 times), brine, dried (MgSO4) and evaporated in vacuo to obtain N-carbomethoxymethyl 2-phenyl-3-[4-((N-methyl-N-phenethyl)carbamoylmethyl)phenyl]propanamide. This is confirmed by NMR and IR, purified by column chromatography using 3:1/EtOAc:hexane and used directly in the next step.

Step B: N-carboxymethyl 2-phenyl-3-[4-((N-methyl-N-phenethyl)carbamoylmethyl)phenyl]propanamide The product of Step A is hydrolyzed according to the procedure of Example 1, Step C to obtain N-carboxymethyl 2-phenyl-3-[4-((N-methyl-N-phenethyl)carbamoylmethyl)phenyl]propanamide. This is purified by column chromatography using 5% MeOH in CHCl$_3$ and identified by NMR and IR.

|   | Calc'd | Found |
|---|--------|-------|
| C | 73.34  | 70.79 |
| H | 6.59   | 6.73  |
| N | 6.11   | 6.36  |

EXAMPLE 13

N-methyl 4-phenyl-5-4-((N-methyl-N-phenethyl)carbamoylmethyl)phenyl]pent-4-enamide N-methyl 4-phenyl-5-4-((N-methyl-N-phenethyl)carbamoylmethyl)phenyl]pentanamide A solution of 4-phenyl-5-[4-((N-methyl-N-phenethyl)carbamoylmethyl)phenyl]pent-4-enoic acid (0.6 g, 1.4 mmol) in CH$_2$Cl$_2$ (20 ml) is treated with carbonyldiimidazole (0.25 g, 1.5 mmol). This is stirred for 5 hours at room temperature and then evaporated to remove the solvent. To this is added a solution of methylamine (40% aqueous solution, 1 ml) in THF (5 ml). This is stirred overnight at room temperature, poured into H$_2$O and made acid with diluted HCl. This mixture is extracted with EtOAc, washed with brine, dried (MgSO$_4$) and evaporated in vacuo to obtain N-methyl 4-phenyl-5-[4-((N-methyl-N-phenethyl)carbamoylmethyl)phenyl]pent-4-enamide which is confirmed by NMR and used directly as follows.

This amide is dissolved in EtOH (50 ml) and reduced with H$_2$ using 0.11 g of 10% Pd-C catalyst and 45 psi. After 4 hours the mixture is filtered through celite, washed with EtOAc and evaporated to dryness to obtain N-methyl 4-phenyl-5-[4-((N-methyl-N-phenethyl)-carbamoylmethyl)phenyl]pentanamide. Purification is by column chromatography using 5% MeOH/CHCl$_3$ and the structure is confirmed by NMR.

|   | Calc'd | Found |
|---|--------|-------|
| C | 78.70  | 76.00 |
| H | 7.74   | 7.68  |
| N | 6.33   | 6.21  |

EXAMPLE 14

N-phenylsulfonyl 4-phenyl-5-4-((N-methyl-N-phenethyl)carbamoylmethyl)phenyl]pentanamide A solution of 4-phenyl-5-[4-((N-methyl-N-phenethyl)carbamoylmethyl)phenyl]pentanoic acid (0.75 g, 1.75 mmol) in CH$_2$Cl$_2$ (15 ml) is treated with 1-(3-dimethylaminopropyl)-3-ethylcarbodiimide·HCl (0.34 g, 1.75 mmol), DMAP catalytic amount) and benzene sulfonamide (0.55 g, 3.5 mmol). This is allowed to stir overnight at room temperature. The solvent is removed and 1N HCl (50 ml) added and the reaction mixture extracted with EtOAc (100 ml). The EtOAc layer is dried (MgSO$_4$) and evaporated to dryness in vacuo. The residue is chromatographed using 2:1/EtOAc:hexane to give N-phenylsulfonyl 4-phenyl-5-[4-((N-methyl-N-phenethyl)carbamoylmethyl)phenyl]pentanamide which is confirmed by NMR.

|   | Calc'd | Found |
|---|--------|-------|
| C | 71.79  | 71.72 |
| H | 6.38   | 6.31  |
| N | 4.93   | 5.09  |
| S | 5.64   | 5.65  |

EXAMPLE 15

4-phenyl-5-[5-(3-phenylpiperidin-1-yl-carbomethyl)-phenyl]pentanoic acid

Step A: Methyl 4-phenyl-5-[4-(3-phenylpiperidine-1-yl-carbomethyl)phenyl]pent-4-enoate When the procedure of Example 1, Step B is followed and 3-phenylpiperidine is used in place of N-methyl-N-phenethylamine the product prepared is methyl 4-phenyl-5-[4-(3-phenylpiperidine-1-yl-carbomethyl)phenyl]-pent-4-enoate. This is purified by column chromatography using 4:1/hexane:EtOAc and confirmed by NMR.

Step B: Methyl 4-phenyl-5-4-(3-phenylpiperidin-1-yl-carbomethyl)phenyl]pentanoate Following the procedure of Example 2, the compound of Step A is reduced to methyl 4-phenyl-5-[4-(3-phenylpiperidin-1-yl-carbomethyl)phenyl]pentanoate and confirmed by NMR.

Step C: 4-phenyl-5-[4-(3-phenylpiperidin-1-yl-carbomethyl)phenyl]pentanoic acid

Following the procedure of Example 1, Step C the ester is hydrolyzed to 4-phenyl-5-[4-(3-phenylpiperidin-1-yl-carbomethyl)phenyl]pentanoic acid. NMR confirms this structure.

|   | Calc'd | Found |
|---|--------|-------|
| C | 79.09  | 77.43 |
| H | 7.30   | 7.61  |
| N | 3.07   | 3.07  |

EXAMPLE 16

N-methyl-N-phenethyl-2-[(3-(4-carboxy-2-phenyl)-butyl)pyrrol-1-yl]acetamide

Step A: N-methyl-N-phenethyl-2-[3-formylpyrrol-1-yl]-acetamide

To a solution of 3-formylpyrrole-1-acetic acid in methylene chloride is added 1.1 molar equivalent of 1,1'-carbonyldiimidazole and several mg of 4-dimethylaminopyridine. The resulting mixture is stirred at room temperature for 18 hours and the reaction mixture is diluted with ethyl acetate. Water is added and the layers are separated. The organic layer is washed with brine and water, dried over MgSO$_4$ and concentrated in vacuo. The residue obtained is purified by a silica gel flash column to give N-methyl-N-phenethyl-2-[3-formylpyrrol-1-yl]-acetamide which is used directly in the next step.

Step B: N-methyl-N-phenethyl-2-3-hydroxymethylpyrrol-1-yl]acetamide

To a solution of N-methyl-N-phenethyl-2-[3-formylpyrrol-1-yl]acetamide in methanol, stirred in an ice bath, is added in portions 5 molar equivalents of sodium borohydride. The mixture is stirred in the cooling bath for an additional 45 minutes and 1N aqueous HCl solution is added dropwise until the pH of the mixture is approximately 6–7. The resulting mixture is concentration in vacuo and the residue obtained is partitioned between ethyl acetate and water. The organic layer is dried over MgSO4 and concentrated in vacuo to give N-methyl-N-phenethyl-2-[3-hydroxymethylpyrrol-1-yl]acetamide. This material is used without further purification in the next step.

Step C: N-methyl-N-phenethyl-2-[3-chloromethyloyrrol-1-yl]acetamide

To a solution of N-methyl-N-phenethyl-2-[3-hydroxymethylpyrrol-1-yl]acetamide and pyridine in methylene chloride is added dropwise 2 molar equivalents of thionyl chloride. The resulting mixture is stirred at room tenperature for 18 hours and ethyl acetate is added. The solution is washed with water and brine, dried over MgSO4 and concentrated in vacuo. The residue obtained is purified by a silica gel flash column to give N-methyl-N-phenethyl-2-[3-chloromethylpyrrol-1-yl]acetamide which is used directly in the next step.

Step D: N-methyl-N-phenethyl-2-(3-(4-carbomethoxy-2-phenyl)buten-1-yl)pyrrol-1-yl]acetamide A solution of N-methyl-N-phenethyl-2-[3-chloromethylpyrrol-1-yl]acetamide and a molar equivalent of triphenylphosphine in toluene is heated to reflux for 6 hours. After cooling to room temperature, the precipitate formed is collected by filtration and dried in vacuo to give the phosphonium chloride Wittig reagent. The phosphonium chloride in N,N-dimethylformamide (DMF) is treated with NaH, followed by an equal molar of methyl 3-benzoylproprionate. The resulting mixture is heated at ~70° C. for several hours, cooled to room temperature and worked up in the usual manner to give crude N-methyl-N-phenethyl-2-[(3-(4-carbomethoxy-2-phenyl)buten-1-yl)pyrrol-1-yl]acetamide which is purified by a silica gel flash column and then used directly in the next step.

Step E: N-methyl-N-phenethyl-2-(3-(4-carbomethoxy-2-phenyl)butyl)pyrrol-1-yl]acetamide A mixture of N-methyl-N-phenethyl-2-[(3-(4-carbomethoxy-2-phenyl)buten-1-yl)pyrrol-1-yl]acetamide and 5% palladium on activated carbon (~0.5 equivalent by weight) in ethyl acetate is shaken on a Parr apparatus under 35 psi of hydrogen for 30 minutes. After the catalyst is removed by filtration, the filtrate is concentrated in vacuo to give N-methyl-N-phenethyl-2-[(3-(4-carbomethoxy-2-phenyl)butyl)pyrrol-1-yl]acetamide which is used directly in the next step.

Step F: N-methyl-N-phenethyl-2-(3-(4-carboxy-2-phenyl)butyl)pyrrol-1-yl]acetamide A solution of N-methyl-N-phenethyl-2-[(3-(4-carbomethoxy-2-phenyl)butyl)pyrrol-1-yl]acetamide in a solvent mixture of methanol-tetrahydrofuran-water (1:1:1, v/v) is treated at room temperature with 5 molar equivalents of LiOH monohydrate for 7 hours. The reaction mixture is concentrated in vacuo and water is added. The resulting solution is extracted with ether, the aqueous layer is acidified with 1N aqueous HCl to pH of 4. The precipitate formed is extracted into ethyl acetate. The organic, solution is washed with brine, dried over MgSO4 and concentrated in vacuo to give N-methyl-N-phenethyl-2-[(3-(4-carboxy-2-phenyl)butyl)pyrrol-1-yl]acetamide.

EXAMPLE 17

4-phenyl-5-2-((N-methyl-N-phenethyl) carbamoylmethyl)pyridin-5-yl]pentanoic acid Step A: 2-chloro-5-(triphenylohosphoniumchloride)-methylpyridine Triphenylphosphine (125 mmol), 2-chloro-5-(chloromethyl)pyridine (100 mmol) and anhydrous toluene (250 ml) are combined. After heating at reflux for 16 hours the reaction mixture is filtered and the solid allowed to air dry to give 2-chloro-5-(triphenylphosphoniumchloride)methylpyridine.

Step B: 4-phenyl-5-(2-chloro)pyridin-5-yl]cent-4-enoic acid

To a mixture of sodium hydride (75 mmol) in anhydrous DMF 2-chloro-5-(triphenylphosphoniumchloride)methylpyridine (75 mmol) is added portionwise. After stirring at ambient temperature for 1 hour, the sodium salt of 3-benzoylpropanoic acid (75 mmol) is added and the reaction heated at 100° C. After 28 hours at 100° C., the reaction mixture is allowed to cool to ambient temperature, poured into water (500 ml) and extracted with ethyl acetate. The ethyl acetate layer is dried (MgSO4) and the solvent removed in vacuo. The residue is chromatographed using silica gel and eluted with hexane:EtOAc to give 4-phenyl-5-[(2-chloro)pyridin-5-yl]pent-4-enoic acid which is used directly in the next step.

Step C: 4-phenyl-5-[2-(t-butyl methyl malonate)pyridin-5-yl]pent-4-enoic acid

To a mixture of sodium hydride (75 mmol) in anhydrous THF (100 ml), t-butyl methyl malonate (75 mmol) is added dropwise. After stirring at ambient temperature for 30 minutes, the sodium salt of 4-phenyl-5-[(2-chloro)pyridin-5-yl]pent-4-enoic acid (60 mmol) is added. The reaction is heated at reflux for 16 hours and the solvent removed. The residue is diluted with 1M HCl, the pH adjusted to 6 with NaHCO3, and the suspension extractracted with EtOAc. The EtOAc solution is dried (MgSO4) and the solvent removed to give 4-phenyl-5-[2-(t-butyl methyl malonate)pyridin-5-yl]pent-4-enoic acid which is used directly in the next step.

Step D: 4-phenyl-5-[2-(carbo-t-butyoxymethyl)pyridin-5-yl]pent-4-enoic acid

A solution of 4-phenyl-5-[2-(t-butyl methyl malonate)pyridin-5-yl]pent-4-enoic acid (50 mmol), methanol (100 ml), lithiumhydroxide (250 mmol) and water (5 ml) are stirred for 6 hours. The solvent is removed and the residue diluted with 1N HCl and the pH adjusted to 6 with 5% NaHCO3 solution. The aqueous mixture is extracted with ethyl acetate which is then dried (MgSO4) and the solvent removed. The residue is heated at 140° C. under argon for 15 minutes. This gives 4-phenyl-5-[2-(carbo-t-butoxymethyl)pyridin-5-yl]pent-4-enoic acid which is used without further purification.

Step E: Methyl 4-phenyl-5-2-carbo-t-butoxymethyl)-pyridin-5-yl]pent-4-enoate

To a solution of 4-phenyl-5-[2-(carbo-t-butoxymethyl)pyridin-5-yl]pent-4-enoic acid (50 mmol) in methylene chloride (250 ml) 1,1'-carbondiimidazole (55 mmol) is added. After 1 hour, methanol (10 ml) is added. The solvent is then removed after 3 hours and the residue chromatographed using silica gel with EtOAc and hexane to give methyl 4-phenyl-5-[2-carbo-t-butoxymethyl)pyridin-5-yl]pent-4-enoate which is used directly in the next step.

Step F: Methyl 4-phenyl-5-2-((N-methyl-N-phenethyl)carbamoylmethyl)pyridin-5-yl]pent-4-enoate A solution of methyl 4-phenyl-5-[2-carbo-t-butoxymethyl)pyridin-5-yl]pent-4-enoate (25 mmol) is stirred in a solution of trifluoroacetic acid/methylene chloride (1:1, 10 ml) for 3 hours. The solvent is removed and the residue diluted in methylene chloride (200 ml), then triethylamine (50 mmol) and 1,1'-carbonyldiimidazole (20 mmol) are added. After 1 hour, N-methyl phenethylamine (50 mmol) is added. The reaction is stirred for 18 hours and the solvent is removed. The residue is diluted with ethyl acetate and washed with 1N HCl, saturated NaCl, 5% NaHCO$_4$ and dried (MgSO$_4$). The solvent is removed by evaporation in vacuo and the residue purified by chromatography using silica gel EtOAc:hexane to give methyl 4-phenyl-5-[2-((N-methyl-N-phenethyl)carbamoylmethyl)pyridin-5-yl]pent-4-enoate which is used directly in the next step.

Step G: 4-phenyl-5-[2-((N-methyl-N-phenethyl)carbamoylmethyl)pyridin-5-yl]pentanoic acid A mixture of methyl 4-phenyl-5-[2-((N-methyl-N-phenethyl)carbamoylmethyl)pyridin-4-yl]pent-4-enoate (20 mmol), 10% palladium on carbon and absolute ethanol (50 ml) are shaken under hydrogen (30 psi). After 3 hours, the mixture is filtered through celite and the solvent removed from the filtrate. The residue is dissolved in methanol (100 ml). Lithium hydroxide (100 mmole) and water (5 ml) are added and the solution stirred for 6 hours. The solvent is removed and the residue diluted with 1N HCl. The aqueous mixture is neutralized to pH 6 with 5% sodium bicarbonate and extracted with ethyl acetate. The ethyl acetate solution is dried (MgSO$_4$) and the solvent removed by evaporation in vacuo to give 4-phenyl-5-[2-((N-methyl-N-phenethyl)-carbamoylmethyl)pyridin-5-yl]pentanoic acid.

EXAMPLE 18

4-phenyl-5-1-((N-methyl-N-phenethyl)carbamoylmethyl)indol-5-yl]pentanoic acid

Step A: Preparation of Wittig reagent N-(2-acetic acid)-5-bromomethylindole

To a mixture of 1 equivalent of sodium hydride in THF (150 ml) is added 5-methylindole (100 mmol) in small portions. After gas evolution ceases, methyl 2-chloroacetate (100 mmol) is added and the reaction mixture stirred at ambient temperature overnight. The reaction is then poured into 500 ml of 2N NaOH solution and stirred until saponification is complete. The basic solution is washed once with Et$_2$O, then made acidic (pH 3) with concentrated HCl, and extracted with EtOAc. The EtOAc extracts are washed with H$_2$O, dried and evaporated to dryness. This residue is then dissolved in CCl$_4$ (500 ml) and N-bromosuccinimide (50 mmol) and a catalytic amount of benzoyl peroxide are added. The mixture is illuminated with a sunlamp for 1½ hours then filtered through silica, extracted with H$_2$O, dried and evaporated. The crude N-(2-acetic acid)-5-bromomethylindole is taken up in toluene (100 ml) and heated at reflux with triphenylphosphine (50 mmol). After the consumption of the bromide, the reaction mixture is cooled to ambient temperature, filtered and the Wittig reagent carried into the next step without further purification.

Step B: 4-phenyl-5-[1-((N-methyl-N-phenethyl)carbamoylmethyl)indol-5-yl]pentanoic acid To a suspension of 2 equivalents of NaH in DMF (30 ml) is added the Wittig reagent of Step A (25 mmol) and the mixture heated at 75° C. for 20 minutes. After this time, ethyl 3-benzoylpropanoate is added and the reaction stirred at 75° C. for 24 hours. The reaction is poured into H$_2$O and the basic solution washed with Et$_2$O. The aqueous suspension is made acidic with 1N HCl (pH 4), then the product extracted with EtOAc. The extract is washed with H$_2$O, dried (MgSO$_4$), evaporated and then applied to a silica gel column and eluted with a mixture of methanol and chloroform. The collected material is evaporated to dryness in vacuo then dissolved in EtOH and shaken under an atmosphere of H$_2$ in the presence of 10% Pd-C. When reaction is complete, the mixture is purged with argon gas, filtered through a pad of celite and evaporated. The resulting material (10 mmol) is taken up in CH$_2$Cl$_2$ and 1 equivalent of carbonyl diimidazole added. This mixture is stirred for 1 hour, then N-methyl-N-phenylethylamine is added. The reaction is stirred at ambient temperature for 18hours, then washed with H$_2$O, dried and evaporated. The residue is diluted with EtOH and 2N NaOH solution (10 ml) added. When saponification of the ester is complete, the reaction mixture is evaporated, 1N HCl added, the resulting solid filtered to obtain 4-phenyl-5-[1-((N-methyl-N-phenethyl)carbamoylmethyl)indol-5-yl]pentanoic acid which is purified by precipitation from EtOAc/petroleum ether.

EXAMPLE 19

4-phenyl-5-[5-((N-methyl-N-phenethyl)carbamoylmethyl)napth-1-yl]pentanoic acid

Step A: 2-(5-methylnaphth-1-yl)acetic acid

A mixture of 1,5-dimethylnaphthylene (200 mmol), N-bromosuccinimide (200 mmol), and a catalytic amount of benzoyl peroxide in CCl$_4$ (700 ml) is illuminated with a sunlamp for 1½ hours. After this time all of the N-bromosuccinimide is consumed and the reaction mixture filtered through silica, washed several times with H$_2$O, dried (MgSO$_4$) and evaporated. The resulting crude monobromination product is diluted with DMF (50 ml) and solid KCN (220 mmol) added. This slurry is heated at 75° C. until reaction is complete. The reaction mixture is poured into H$_2$O and this emulsion extracted twice with Et$_2$O. The Et$_2$O extracts are washed several times with H$_2$O, then dried and evaporated. The crude acetonitrile derivative is refluxed in a 1:1 mixture of ethanol:aqueous 20% KOH solution. When the reaction is complete, the mixture is evaporated, 3N HCl solution (250 ml) added and the suspension extracted with EtOAc. The EtOAc extracts are washed with H$_2$O, dried and evaporated. The residue is chromatographed on silica gel by elution with EtOAc/petroleum ether to give pure 2-(5-methylnaphth-1-yl)acetic acid which is used directly in the next step.

Step B: Preparation of the Wittig reagent of 2-(5-bromomethylnapth-1-yl)acetic acid 2-(5-methylnaphth-1-yl)acetic acid (50 mmol) is dissolved in CCl$_4$ (500 ml) and a small amount of benzoyl peroxide added. This mixture is illuminated with a sunlamp and a solution Br$_2$ (45 mmol) in CCl$_4$ (200 ml) added over a 4 hour period. After this time the reaction is filtered through silica, dried and evaporated. The crude 2-(5-bromomethylnaphth-1-yl)acetic acid is taken up in toluene (100 ml), then heated at reflux with triphenylphosphine (50 mmol). After the consumption of the bromide, the reaction mixture is cooled to ambient temperature, filtered and the Wittig reagent carried into the next step without further purification.

Step C: 4-phenyl-5-5-((N-methyl-N-phenethyl)carbamoylmethyl) napth-1-yl]pentanoic acid To a suspension of 2 equivalents of NaH in DMF (30 ml) is added 25 mmol of the Wittig reagent of Step B and the mixture heated at 75° C. for 20 minutes. After this time, ethyl 3-benzoylpropanoate is added and the reaction stirred at 75° C. for 24 hours. The reaction is poured into H₂O and the basic solution washed with Et₂O. The aqueous suspension is made acidic with 1N HCl (pH 4), then the product extracted with EtOAc. The extract is washed with H₂O, dried (MgSO₄), evaporated and then applied to a silica gel column and eluted with a mixture of methanol and chloroform. The material collected is evaporated to dryness in vacuo and then dissolved in EtOH and shaken under an atmosphere of H₂ in the presence of 10% Pd-C. When the reaction is complete, the mixture is purged with argon gas, filtered through a pad of celite and evaporated. The resulting material (10 mmol) is taken up in CH₂Cl₂ and 1 equivalent of carbonyl diimidazole added. This mixture is stirred for 1 hour and N-methyl-N-phenylethyl amine is added. The reaction is stirred at ambient temperature for 18 hours, washed with H₂O, dried and evaporated. The residue is diluted with EtOH and 2N NaOH solution (10 ml) is added. When saponification of the ester is complete, the reaction mixture is evaporated, 1N HCl is added and the resulting solid is filtered to obtain 4-phenyl-5-[5-((N-methyl-N-phenethyl)carbamoyl-methyl)-napth-1-yl]pentanoic acid which is purified by precipitation from EtOAc/petroleum ether.

EXAMPLE 20

The structures of the foregoing compounds are routinely verified by analytical procedures including NMR, IR, UV, mass spec. and elemental analyses.

We claim:

1. A compound of the formula

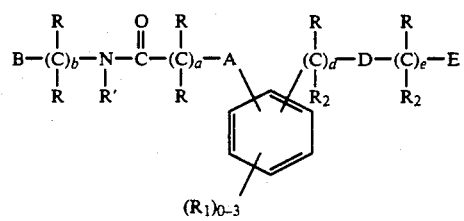

where:

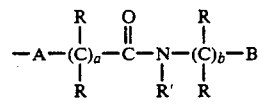

is selected from

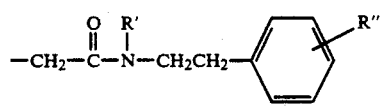

and

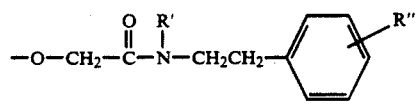

where R' is hydrogen or lower alkyl (having about 1 to about 6 carbon atoms) and R" is hydrogen, lower alkyl (having about 1 to about 6 carbon atoms) or lower alkoxy (having about 1 to about 6 carbon atoms);

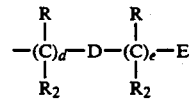

is selected from $(CHR_2)_d$—E where d is 0–4, —$(CR_2=CR_2)_x$—E where x is 1–2, —O—$(CHR_2)_d$—E where d is 1–3, —$(CHR_2)_d$—$CR_2=CR_2$—E where d is 1–3 and —O—$(CHR_2)_d$—$CR_2=CR_2$—R where d is 1–3, R₁ is hydrogen;

R₂ is hydrogen, lower alkyl (having about 1 to about 6 carbon atoms) and at least one of R₂ is selected from

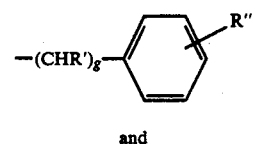

and

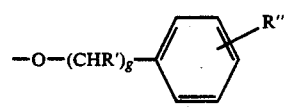

where g is 0–3, R' is hydrogen or lower alkyl (having about 1 to about 6 carbon atoms) and R" is hydrogen, lower alkyl (having about 1 to about 6 carbon atoms) or lower alkoxy (having about 1 to about 6 carbon atoms); and

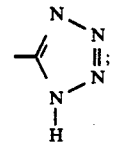

E is —COOH or;

or an isomer or a pharmaceutically acceptable salt thereof.

2. A compound according to claim 1 where the substituents are in the 1,3 or 1,4 positions of the phenyl ring.

3. A compound according to claim 2 which is 4-phenyl-5-4-((N-methyl-N-phenethyl)carbamoylmethyl)-phenyl]-E-pent-4-enoic acid.

4. A compound according to claim 2 which is 4-phenyl-5-4-((N-methyl-N-phenethyl)carbamoylmethyl)-phenyl]-Z-pent-4-enoic acid.

5. A compound according to claim 2 which is 4-phenyl-5-4-((N-methyl-N-phenethyl)carbamoylmethyl)-phenyl]pentanoic acid.

6. A compound according to claim 2 which is 5-[4-((4-(N-methyl-N-phenethyl)carbamoylmethyl)phenyl)-3-phenylbutyl]-H-tetrazole.

7. A compound according to claim 2 which is 4-phenyl-5-4-((N-methyl-N-phenprop-2-yl)carbamoylmethyl)phenyl]-pentanoic acid.

8. A compound according to claim 2 which is 4-phenyl-5-4-((N-methyl-N-phenprop-2-yl)carbamoylmethyl)phenyl]-E-pent-4-enoic acid.

9. A compound according to claim 2 which is 4-phenyl-5-4-((N-methyl-N-phenprop-2-yl)carbamoylmethyl)phenyl]-Z-pent-4-enoic acid.

10. A compound according to claim 2 which is 4-phenyl-5-4-((N-propyl-N-phenethyl)carbamoylmethyl)-phenyl]pentanoic acid.

11. A compound according to claim 2 which is 4-phenyl-5-4-((N-methyl-N-phenethyl)carbamoylmethyl)-phenyl]pent-2-enoic acid.

12. A compound according to claim 2 which is 2-phenyl-3-[4-((N-methyl-N-phenethyl)carbamoylmethyl)-phenyl]propanoic acid.

13. A compound according to claim 2 which is 6-phenyl-7-[4-((N-methyl-N-phenethyl)carbamoylmethyl)-phenyl]hept-2-enoic acid.

14. A compound according to claim 2 which is 6-phenyl-7-[4-((N-methyl-N-phenethyl)carbamoylmethyl)-phenyl]heptanoic acid.

15. A compound according to claim 2 which is 2-methyl-4-phenyl-5-[4-((N-methyl-N-phenethyl)carbamoylmethyl)phenyl]-pentanoic acid.

16. A compound according to claim 2 which is 2-methyl-4-phenyl-5-[4-((N-methyl-N-phenethyl)carbamoylmethyl)phenyl]-pent-2-enoic acid.

17. A method for the treatment of hypersensitive ailments in humans and mammals comprising administering thereto an effective anti-hypersensitive amount of a compound of the formula according to claim 7.

18. A method for the treatment of inflammatory diseases in humans and mammals comprising administering thereto an effective anti-inflammatory amount of a compound of the formula according to claim 7.

19. A method according to claim 18 where the inflammatory disease is inflammatory bowel disease.

20. A pharmaceutical-composition wherein the active ingredient is a compound according to claim 7 in admixture with a pharmaceutical carrier.

* * * * *